(12) United States Patent
Hess et al.

(10) Patent No.: US 10,568,724 B2
(45) Date of Patent: Feb. 25, 2020

(54) TOOTHBRUSH COMPRISING ASYMMETRICALLY ORIENTED TUFTS OF BRISTLES

(71) Applicant: TRISA HOLDING AG, Triengen (CH)

(72) Inventors: Walter Hess, Obernau (CH); Patrik Steinmann, Neuenkirch (CH)

(73) Assignee: TRISA HOLDING AG, Triengen (CH)

( * ) Notice: Subject to any disclaimer, the term of this patent is extended or adjusted under 35 U.S.C. 154(b) by 351 days.

(21) Appl. No.: 15/403,878

(22) Filed: Jan. 11, 2017

(65) Prior Publication Data

US 2017/0172716 A1    Jun. 22, 2017

Related U.S. Application Data

(62) Division of application No. 13/817,310, filed as application No. PCT/EP2011/001144 on Mar. 9, 2011, now Pat. No. 9,572,417.

(30) Foreign Application Priority Data

Aug. 18, 2010    (EP) .................................... 10008599

(51) Int. Cl.

| A61C 17/22 | (2006.01) |
|---|---|
| A61C 17/34 | (2006.01) |
| A46B 3/16 | (2006.01) |
| A46B 9/02 | (2006.01) |
| A46D 3/04 | (2006.01) |

(Continued)

(52) U.S. Cl.
CPC .............. *A61C 17/222* (2013.01); *A46B 3/16* (2013.01); *A46B 9/025* (2013.01); *A46B 9/028* (2013.01); *A46B 9/04* (2013.01); *A46D 3/00* (2013.01); *A46D 3/042* (2013.01); *A46D 3/082* (2013.01); *A61C 17/22* (2013.01);

(Continued)

(58) Field of Classification Search
CPC ... A61C 17/22; A61C 17/222; A61C 17/3445; A61C 17/3472; A61C 17/3481
See application file for complete search history.

(56) References Cited

U.S. PATENT DOCUMENTS

| 5,500,975 A | 3/1996 | Sano |
| 5,504,959 A * | 4/1996 | Yukawa ............. A61C 17/3472 |
| | | 15/22.1 |

(Continued)

FOREIGN PATENT DOCUMENTS

| DE | 195 16 356 A1 | 11/1996 |
| DE | 19832436 A1 | 1/2000 |

(Continued)

OTHER PUBLICATIONS

Feb. 19, 2013 International Preliminary Report on Patentability issued in International Application No. PCT/EP2011/001144.

(Continued)

*Primary Examiner* — Randall E Chin
(74) *Attorney, Agent, or Firm* — Oliff PLC

(57) ABSTRACT

A toothbrush includes a handle and a bristle-carrying head part, which are connected to each other by a neck part, the head part having a multiplicity of tufts of bristles consisting of bristles. An anchor is oriented at right angles to the longitudinal axis. Two or more tufts of bristles have a bristle tuft half with bristle ends standing up higher in relation to the bristle ends of the other bristle tuft half.

16 Claims, 11 Drawing Sheets

(51) Int. Cl.
  *A46B 9/04* (2006.01)
  *A46D 3/00* (2006.01)
  *A46D 3/08* (2006.01)

(52) U.S. Cl.
  CPC ...... *A61C 17/3445* (2013.01); *A61C 17/3472* (2013.01); *A61C 17/3481* (2013.01); *A46B 2200/1066* (2013.01)

(56) References Cited

U.S. PATENT DOCUMENTS

| | | | |
|---|---|---|---|
| 5,542,749 | A | 8/1996 | Toth |
| 5,926,897 | A | 7/1999 | Volpenhein |
| 6,044,514 | A | 4/2000 | Kaneda et al. |
| D425,306 | S | 5/2000 | Beals et al. |
| 6,202,241 | B1 * | 3/2001 | Hassell ............ A46B 9/045 15/167.1 |
| 6,412,139 | B1 | 7/2002 | Weihrauch |
| 8,029,069 | B2 | 10/2011 | Kwon et al. |
| 8,185,993 | B2 | 5/2012 | Fischer et al. |
| 2009/0183324 | A1 * | 7/2009 | Fischer ............ A61C 17/34 15/22.1 |

FOREIGN PATENT DOCUMENTS

| | | |
|---|---|---|
| EP | 0 360 766 A1 | 3/1990 |
| EP | 0 433 470 A1 | 6/1991 |
| EP | 1425989 A1 | 6/2004 |
| JP | S57-134113 A | 8/1982 |
| JP | 2000-296024 A | 10/2000 |
| JP | 2001-178542 A | 7/2001 |
| JP | 2001-353026 A | 12/2001 |
| WO | 97/42853 A1 | 11/1997 |
| WO | 98/05238 A1 | 2/1998 |
| WO | 2008/081697 A1 | 7/2008 |
| WO | 2009/000903 A1 | 12/2008 |
| WO | 2009/084637 A1 | 7/2009 |

OTHER PUBLICATIONS

Oct. 14, 2011 Written Opinion of the International Searching Authority issued in International Application No. PCT/EP2011/001144.
Apr. 29, 2011 European Search Report issued in European Application No. 10 00 8599.
May 19, 2015 Office Action issued in European Patent Application No. 11 708 407.9.

* cited by examiner

TOOTHBRUSH COMPRISING ASYMMETRICALLY ORIENTED TUFTS OF BRISTLES

This application is a divisional application of application Ser. No. 13/817,310 filed Feb. 15, 2013, now U.S. Pat. No 9,572,417 which in turn is a U.S. national stage application of PCT/EP 2011/001144 filed Mar. 9, 2011. Each of the prior applications is incorporated herein by reference in its entirety.

BACKGROUND

The present invention concerns a toothbrush and a process for producing a toothbrush.

Toothbrushes usually have a brush head with a bristle area formed by tufts of bristles. Such toothbrushes have long been known. Over the course of time, the bristle areas of such toothbrushes have undergone varied designs and further developments to improve on the one hand the cleaning effect and on the other hand the comfort or convenience for the user. One of these developments concerns the use of profiled bristle areas and tufts of bristles with bristles standing up to different heights in the tuft of bristles.

The document U.S. Pat. No. 5,926,897 discloses a toothbrush with a bristle area consisting of tufts of bristles. This bristle area is of a profiled configuration and the individual tufts of bristles have a number of bristles standing up higher, which form a higher end area.

The document DE 198 32 436 describes a process for producing brushes, in particular toothbrushes. The process shows the working of tufts of bristles with bristles of different lengths, the working of the bristles being carried out in various steps by means of lateral deflection.

US Design 425,306 shows an ornamental bristle area with substantially triangular tufts of bristles, at the corners of which higher bristles are arranged.

The document EP 1 425 989 discloses toothbrushes with pointed bristles and a process for producing the same. The bristles may in this case have two identical pointed ends or different ends, that is to say a non-pointed end and a pointed end.

The document WO 2009/000903 describes a toothbrush with tufts of bristles which have on the one hand shorter, non-pointed bristles and on the other hand longer, pointed bristles. The longer bristles may be randomly distributed in the tuft of bristles or arranged centrally in an inner region of the tuft of bristles.

Various efforts aimed at providing toothbrushes which comprise a bristle area that has bristles with bristle ends standing up to different heights in a tuft of bristles are known from the prior art. However, the corresponding processes are complex or only allow a restricted design of the bristle area.

SUMMARY

The present invention is therefore based on the object of providing a toothbrush which comprises an improved cleaning effect, in particular of the interdental spaces, while the toothbrush is produced as simply as possible in a process that is as reliable as possible.

The object is achieved by a toothbrush as described herein and a process with the features described herein.

A toothbrush according to the invention has a handle and a bristle-carrying head part. The handle and the head part are connected to each other by means of a neck part. The head part carries the bristles and consequently has tufts of bristles, which for their part comprise a multiplicity of bristles or bristle filaments. The expressions bristle, filament and bristle filament are used synonymously hereafter and refer to an individual bristle filament. These bristle filaments are produced by means of an extrusion process and are cut to the correct length before they are fixed on the toothbrush. For this reason, in their unworked state, the bristle filaments have a cylindrical cross section. This cross section is usually circular, but may also have a form deviating from a circle.

With preference, the bristles or the tufts of bristles extend in a perpendicular direction away from the head part. In an alternative embodiment, the tufts of bristles according to the invention may also extend from the head at an angle. At least two of the tufts of bristles of the head part comprise at least one bristle which has a bristle end that stands up higher in relation to the bristle ends of the other bristles of the tuft of bristles. The at least one bristle with the higher bristle end is arranged non-centrally within the tuft of bristles. If a number of bristles with a higher bristle end are present, they are also arranged non-centrally within the tuft of bristles comprising them. Furthermore, the at least two tufts of bristles which comprise at least one bristle with a higher bristle end are preferably arranged on opposite sides of an (imaginary) central longitudinal plane of the toothbrush.

The (imaginary) central longitudinal plane is at right angles to the bristle area in the head of the toothbrush. Moreover, the central longitudinal plane runs through the longitudinal axis of the toothbrush. All the tufts of bristles of the head part preferably run at least approximately parallel to the central longitudinal plane.

The two or more tufts of bristles that have at least one bristle with a higher bristle end are arranged on the opposite sides of the central longitudinal plane in such a way that one half, which comprises at least one bristle with an end standing up higher, is oriented toward the central longitudinal plane. Alternatively, the converse arrangement is also possible, so that the ends standing up higher are oriented away from the central longitudinal plane.

In an alternative embodiment, the toothbrush according to the invention has the following features: a toothbrush with a handle and a bristle-carrying head part, which are connected to each other by a neck part, the head part having a multiplicity of tufts of bristles consisting of bristles, two or more tufts of bristles having at least one bristle with a bristle end standing up higher in relation to the bristle ends of the other bristles, the at least one bristle with a higher bristle end being arranged non-centrally within the tuft of bristles, and the two or more tufts of bristles being arranged on opposite sides of a central longitudinal plane of the toothbrush and all the tufts of bristles being oriented uniformly with one half of the tuft of bristles that comprises the at least one bristle with a higher bristle end being oriented toward or alternatively away from the central longitudinal plane.

In a preferred embodiment, the tufts of bristles are fastened on the head part by means of an anchor. Bristling processes which fasten tufts of bristles by means of an anchor in corresponding blind holes of the head part are known per se. By means of the anchor, the tufts of bristles are symmetrically or asymmetrically folded and subsequently fixed in blind holes. The folding by means of the anchor has the effect that the tuft of bristles has two halves (bristle tuft halves), which each comprise one of the ends of the folded bristles.

In a further preferred embodiment, the bristles with a higher bristle end are arranged in the half of the tuft of bristles comprising them substantially in one region of this half. This means that the bristles with a higher bristle end are not randomly distributed within the half of the tuft of bristles comprising them but are substantially concentrated on one region of this half. In this region, there may also be bristles which do not have a higher bristle end.

In a preferred embodiment, all the anchors have the same orientation. They are, for example, aligned parallel to the central longitudinal plane.

In another embodiment, the anchors have at least two orientations. Some of the anchors may, in turn, be oriented parallel to the central longitudinal plane, while others of the anchors are not aligned parallel to the central longitudinal plane but form or include an angle with this plane. This angle is preferably in the range from 0° to 90°, with particular preference in the range from 0° to 30°.

In a preferred embodiment, the two or more tufts of bristles which have at least one bristle with a higher end are arranged mirror-invertedly in relation to the central longitudinal plane.

In a further embodiment, the anchors are oriented substantially perpendicular to the longitudinal axis of the toothbrush. This means that the anchors include an angle with the longitudinal axis of 90°+/−20°, preferably 90°+/−10°. This angle may vary over the tufts of bristles of a toothbrush. In this embodiment it is possible to orient the higher bristle ends in the tufts of bristles the same in each case. Consequently, the higher bristle ends of at least one tuft respectively stand substantially either on the handle side or on the free side of the toothbrush.

Furthermore, the tufts of bristles may be oriented alternately row by row, i.e. the first row of tufts of bristles on the side of the free end of the toothbrush has the lower bristle ends on the side of the free end of the toothbrush. The next row has the higher bristle ends on the side of the free end of the toothbrush. This achieves the effect that the interdental penetration is improved. The distances between the clusters with the higher bristle ends becomes greater, so that the engagement of these becomes better. These tufts of bristles are preferably not thinned out.

Consequently, a symmetrical pattern of the tufts of bristles with respect to the longitudinal center axis of the toothbrush is preferably produced.

It is also possible to combine the stated tuft orientations in one bristle area.

In a further embodiment, bristles that are pointed at one end are used. These are produced from cylindrical bristles, by rounding them at the free end, preferably on the bristle strand, in a first step and subsequently cutting them to the correct length. Alternatively, cut-to-size bristles are rounded at one end of the bristles only after they have been cut from the bristle strand.

Subsequently, they are pointed at the end opposite from the rounded end, and possibly colored. After that, they can be inserted into a toothbrush. In this case, the pointed ends form the higher bristle ends and the rounded ends form the lower bristle ends. The bristles, or tufts of bristles, produced in this way are preferably neither rounded off nor thinned out after anchoring in the brush head.

In the case of a particularly preferred toothbrush with a handle and a bristle-carrying head part, which are connected to each other by a neck part, the head part has a multiplicity of tufts of bristles, consisting of bristles, respectively forming two bristle tuft halves and fastened in the head part by means of an anchor. The anchor of at least one tuft of bristles is oriented at least approximately at right angles to a longitudinal axis of the toothbrush and at least two tufts of bristles have a bristle tuft half with bristle ends standing up higher in relation to the bristle ends of the other bristle tuft half. With particular prefererence, one of these at least two tufts of bristles is the one which is fastened with the anchor oriented at least approximately at right angles to the longitudinal axis of the toothbrush. Further preferred embodiments of this toothbrush are specified in the following paragraphs.

With preference, the bristles are bristles that are pointed at one end.

With preference, the pointed ends of the pointed bristles form the higher bristle ends.

With preference, the anchor of a number of tufts of bristles is oriented at least approximately at right angles to the longitudinal axis of the toothbrush and the relevant bristle tuft halves with the higher bristle ends are facing the neck part and the relevant bristle tuft halves with the lower bristle ends are facing away from the neck part. With particular preference, this applies to all the tufts of bristles.

It is also preferred for the anchor of a number of tufts of bristles to be oriented at least approximately at right angles to the longitudinal axis of the toothbrush and the relevant bristle tuft halves with the higher bristle ends of tufts of bristles neighboring in the direction of the longitudinal axis of the toothbrush to be facing one another. With particular preference, this applies to all the tufts of bristles.

It is also preferred for the anchor of a number of tufts of bristles to be oriented at least approximately at right angles to the longitudinal axis of the toothbrush and for the relevant tufts of bristles to be arranged in rows running transversely to the longitudinal axis of the toothbrush and arranged one behind the other in the direction of the longitudinal axis of the toothbrush. The tufts of bristles are in this case oriented identically in rows and the relevant bristle tuft halves with the higher bristle ends of the tufts of bristles of one row and the relevant bristle tuft halves with the higher bristle ends of a neighboring row are facing one another or facing away from one another. With particular preference, the anchors of all the tufts of bristles are oriented at least approximately at right angles to the longitudinal axis of the toothbrush and the above applies to all the tufts of bristles. Furthermore, with preference, the rows run at right angles to the longitudinal axis of the toothbrush.

In the case of a further preferred embodiment, the anchor of a number of tufts of bristles is oriented at least approximately at right angles to the longitudinal axis of the toothbrush and the relevant bristle tuft halves with the higher bristle ends are facing away from the neck part and the relevant bristle tuft halves with the lower bristle ends are facing the neck part. With preference, this applies to all the anchors and all the tufts of bristles.

In the case of a process for producing an aforementioned particularly preferred toothbrush with a handle and a bristle-carrying head part, which are connected to each other by a neck part, tufts of bristles consisting of a multiplicity of bristles and respectively forming two bristle tuft halves are fastened in blind holes in the head part by means of an anchor. The anchor of at least one tuft of bristles is punched into the head part such that it is oriented at least approximately at right angles to the longitudinal axis of the toothbrush. The bristles of at least two tufts of bristles are folded asymmetrically about the anchor, whereby one bristle tuft half has bristle ends standing up higher in relation to the bristle ends of the other bristle tuft half.

In the case of this process, bristles that are pointed at one end are used with preference as bristles.

With preference, the bristles are pointed and/or rounded at the two bristle ends thereof before they are introduced into the blind holes of the head part.

With preference, these bristles are no longer worked after they have been introduced into the blind holes.

The higher bristle ends are arranged such that they stand up higher in relation to the bristle ends of the other bristles by 0.5 mm to 5 mm. With preference, they are 2 mm to 3 mm higher than the bristle ends of the other bristles.

The tufts of bristles of the head part may comprise bristles with different bristle ends. Apart from cylindrical bristles with rounded-off ends, there may also be bristles with a pointed end. Preferably, the cross section is circular, but may also have a form deviating from a circle.

In another embodiment, the head part has in addition to conventional, extruded bristles with rounded-off or pointed bristle ends, at least one soft-elastic structure. This soft-elastic structure is preferably configured as a cleaning and massaging element. As a difference from the bristles, the soft-elastic structures are preferably produced together with the toothbrush handle by means of an injection-moulding technique, for example in the two- or multi-component injection-molding process.

A device for providing a toothbrush with bristles comprises a tufting device with a bristle feed and a bristle tuft conveyor with a notch. The bristle tuft conveyor is assigned a stop for the tufts of bristles. In this case, the stop and/or the bristle feed are adjustable perpendicularly to a plane of movement of the tuft conveyor.

The stop is in this case preferably adjustable in its height between 2 mm and 30 mm, with particular preference between 4 mm and 10 mm.

To ensure movement of the bristles that is as good as possible, the stop has a polished surface, that is to say a polished supporting surface, in a region in which it comes into contact with bristles.

In a preferred embodiment of the device for providing toothbrushes with bristles, the distance between the supporting surface of the stop and the tuft conveyor is kept constant (parallel planes). This means that the supporting surface of the stop and the tuft conveyor are arranged in parallel planes.

In another embodiment, the distance between the supporting surface of the stop and the tuft conveyor is variable. In this case, the distance A decreases in a direction leading away from the material channel, that is to say the planes are at an angle to each other.

In a process for producing a toothbrush, the toothbrushes are provided with bristles by a device described above.

BRIEF DESCRIPTION OF THE DRAWINGS

The present invention is explained in more detail below with reference to the drawing, in which, purely schematically.

DETAILED DESCRIPTION

Figure 1:
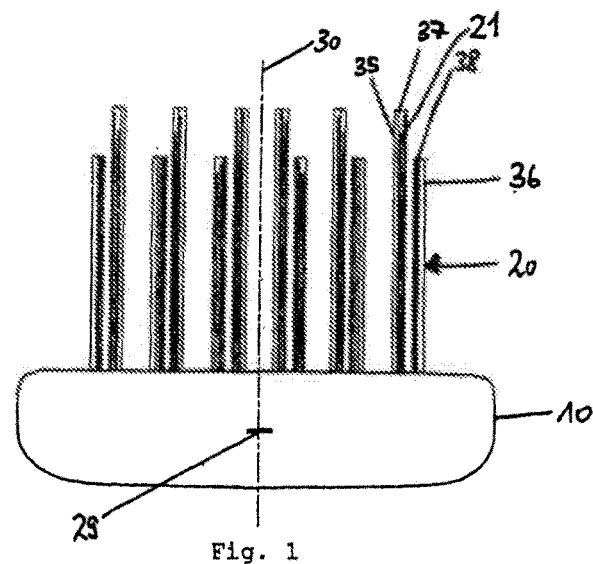
FIG. 1 shows the view of a toothbrush head in the direction of the longitudinal axis of the toothbrush.

FIG. 1 shows a view of a head part 10 of a toothbrush (also referred to herein as a toothbrush head) in the direction of the longitudinal axis 29 of the toothbrush perpendicular to the viewing plane. The tufts of bristles 20 shown are arranged in a transverse row on the head part 10 and extend at least approximately, here exactly, perpendicularly away from the head part 10. The tufts of bristles 20 comprise bristles 21 with a bristle end 37 standing up higher in relation to the other bristles. In the embodiment shown, the bristle tuft half 35 of the tufts of bristles 20 which comprises the bristles 21 with higher bristle ends 37 on the opposite sides of the central longitudinal plane 30 are respectively oriented toward this central longitudinal plane. Accordingly, the majority of the bristles with lower bristle ends 38 are facing away from the central longitudinal plane. The six tufts of bristles 20 shown accordingly have different orientations on the opposite sides of the central longitudinal plane 30, this characteristic being easy to see from the higher bristle ends 37.

The bristles 21 are arranged in this way on the entire toothbrush, apart from tufts of bristles 20 which are arranged on the longitudinal axis 29. The tufts that are arranged on the longitudinal axis 29 may be oriented toward one or the other side of the longitudinal axis or of the central longitudinal plane. In the profile of the bristle ends, the higher position and lower position of certain bristle ends with respect to other bristles produce two levels of ends, the higher bristle ends 37 penetrating into the interdental spaces better than the lower bristle ends 38.

Figures 2, 3:
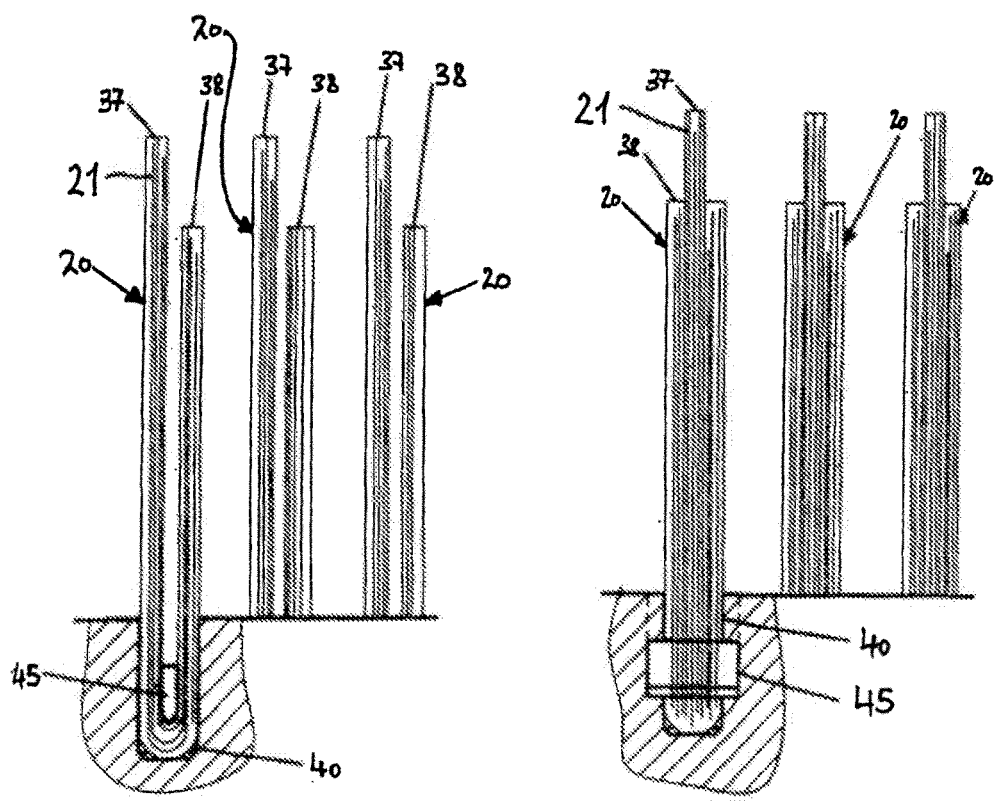
FIG. 2 shows a tuft of bristles in the direction of the longitudinal axis of an anchor.
FIG. 3 shows a tuft of bristles in the transverse direction in relation to the longitudinal axis of the anchor.

In the representation of FIG. 1, and also the subsequent FIG. 2, the spacing brought about by the anchor 45 holding them in the brush head 10 in the known manner is in each case shown as being relatively clear. The drawings are schematic; in reality, the bristles "splay" somewhat and the spacing is no longer visible at the end of the tuft of bristles 20, or even already at the level of the lower bristle ends 38.

A conventional and known process for providing toothbrushes with bristles is that of fastening the tufts of bristles 20 in the head part 10 by means of anchors 45. In FIG. 2, a detailed view of a tuft of bristles 20 is shown in the direction of the longitudinal axis of an anchor 45. The anchor 45 folds the tuft of bristles 20 into two parts. During the tufting of the tufts of bristles 20 in blind holes 40 of the head part that are provided for this purpose, the anchor 45 firmly clamps the bristles 21 in the blind hole. The anchor 45 thereby penetrates into the plastic that surrounds the respective blind hole 40 and in this way anchors itself at the respective position. The bristles 21 are consequently firmly clamped between the wall of the blind hole 40 and certain surfaces of the anchor 45.

In the case of conventional toothbrushes, the folding of the bristles 21 by the anchor 45 takes place symmetrically, that is to say that there is the same length of bristle on both sides of the anchor 45. In the case of the present invention, however, the tufts of bristles 20 are folded asymmetrically. The three tufts of bristles 20 shown, with the higher and lower bristle ends 37, 38, are all oriented identically in the present example, i.e. the higher bristle ends 37 are always obtained on the same side of the anchor 45. It is generally the case that the higher bristle ends 37 are always arranged on the same side of the anchor 45. It is not the case that some of the higher bristle ends are arranged on the left side of the anchor and others are arranged on the right side of the anchor.

FIG. 3 shows tufts of bristles 20 in the transverse direction in relation to the longitudinal axis of the anchor 45. In this case, the section through the blind hole 40 is shown only in the case of one tuft of bristles 20. From this view, in combination with FIG. 2, it becomes clear that only a relatively small number of the bristles 21 of a tuft of bristles 20 have bristle ends 37 which stand up higher in relation to the bristle ends 38 of the other bristles 20. In FIG. 3, it can also be seen well how much the anchor 45 penetrates into the plastic surrounding the blind hole 40. The edge of this trace of the penetration is represented in the figure by dashed lines.

The length ratios in the tufts of bristles 20 of the finished toothbrush are such that, from leaving the blind hole 40 to the higher bristle ends 37, the tuft of bristles 20 has in each case a length of 9 mm to 15 mm, preferably from 10 mm to 12 mm. The length from leaving the blind hole 40 to the lower bristle ends 38 is between 6 mm and 11 mm, preferably 8 mm to 10 mm. The higher bristle ends 37 are arranged such that they stand up higher in relation to the bristle ends 38 of the other bristles by 0.5 mm to 5 mm. With preference, they stand up higher than the bristle ends 38 of the other bristles by 2 mm to 3 mm.

Figure 4:
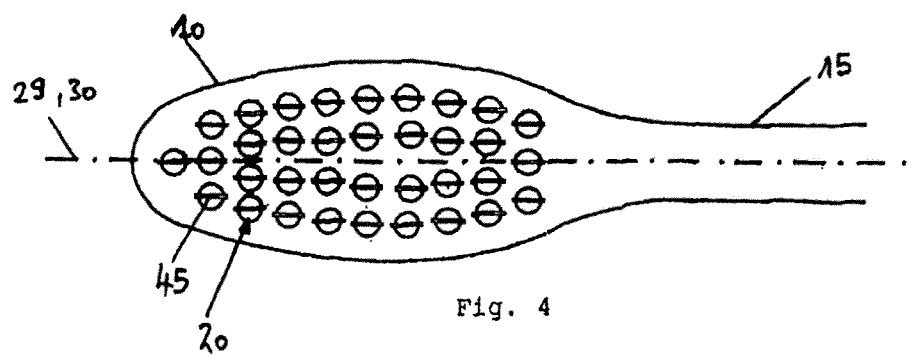
FIG. 4 shows a possible arrangement of the anchors in a head part of a toothbrush, with bristles omitted.

In FIG. 4, a possible arrangement of the anchors 45 by means of which the tufts of bristles 20 are fastened in the head part 10 of the toothbrush is shown. The neck part 15 adjacent the head part 10 is only partially depicted; a handle adjoins the neck part 15 in a known manner.

In the embodiment shown, all the anchors 45 have the same orientation or alignment with respect to the longitudinal center axis 29. In the present example, the angle which is included by the anchor 45 and the longitudinal center axis 29 is 0°. The angle may preferably lie in a range between 0° and 30°.

To embody the invention, the tufts of bristles 20 are arranged on the head part 10 in transverse rows. In FIG. 4, the bristles 21 are not shown for representational reasons.

Figure 5:
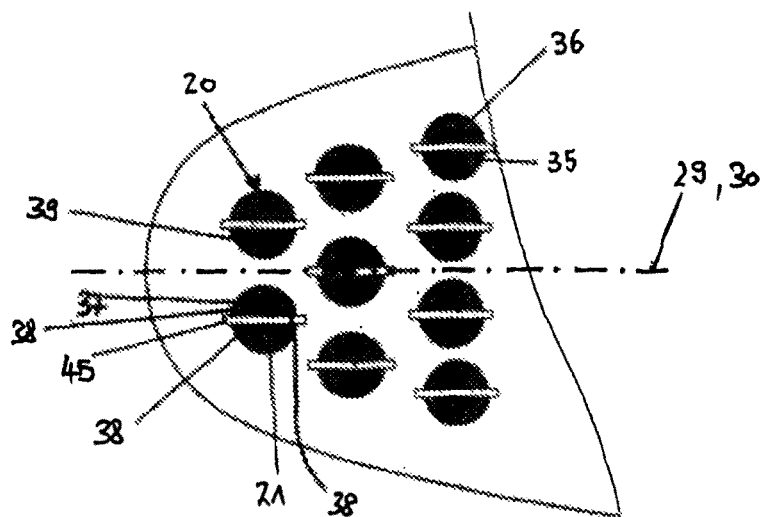
FIG. 5 shows an enlarged representation of the end region of the head part shown in FIG. 4, with bristles represented.

FIG. 5 shows an enlarged representation of the free end region of the head part 10 shown in FIG. 4, this time with bristles 21 shown. The tufts of bristles 20 arranged in transverse rows can in turn be seen.

The anchor 45 of the tuft of bristles 20 divides this tuft of bristles into two halves in plan view. The bristle tuft half 35 of the tuft of bristles 20 that comprises the bristles 21 with higher bristle ends 37 is in this case oriented toward the central longitudinal plane 30. The higher bristles 37 are represented in the figure as shaded. The bristle tuft half 36 of the tuft of bristles 20 that is facing away from the central longitudinal plane 30 only comprises bristles 21 with lower bristle ends 38.

It can likewise be seen in this view that the bristle tuft halves 35 of the tufts of bristles 20 with bristles which have a bristle end 37 standing up higher in relation to the other bristles also comprise bristles with a lower bristle end 38.

In the case of the tufts of bristles 20 arranged on the head part 10 in transverse rows, the anchors 45 aligned parallel to the central longitudinal plane 30 produce a mirror-inverted arrangement of the tufts of bristles 20. Excluded from this are tufts of bristles through which the central longitudinal plane 30 passes. In such tufts of bristles 20, the bristles 21 with higher bristle ends 37 face either one or the other side of the central longitudinal plane 30.

The arrangement of the higher and lower bristle ends 37, 38 is also possible in a conversely oriented manner, so that the higher bristle ends 37 are directed away from the central longitudinal plane 30 and the lower bristle ends 38 are directed toward the central longitudinal plane 30. An important point in this respect is that the anchor 45, which fixes the tufts of bristles in the head part 10, may also assume an angle in relation to the longitudinal axis 29. In this case, one speaks of higher bristle ends 37 oriented toward the central longitudinal plane if they are arranged in the angle, i.e. the area, between 0° and 89.99° between the longitudinal axis of the anchor and the central longitudinal plane 30. Conversely, one speaks of higher bristle ends 37 oriented away from the central longitudinal plane 30 if the lower bristle ends 38 are arranged in the way just described.

Figure 6:
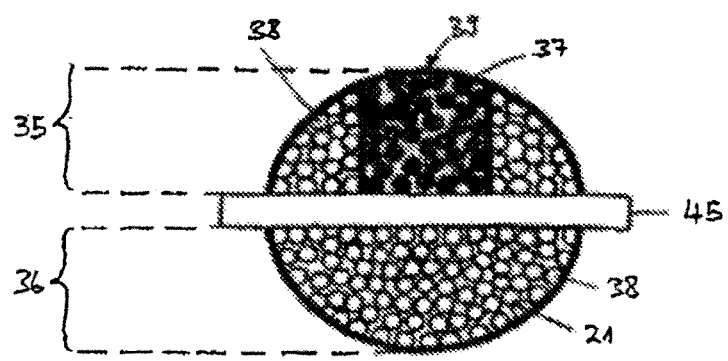
FIG. 6 shows a plan view of an enlarged tuft of bristles from FIG. 5.

FIG. 6 shows a plan view of a single tuft of bristles 20 from FIG. 5, shown enlarged. The anchor 45 divides the tuft of bristles 20 into two bristle tuft halves 35 and 36. In this case, the bristle tuft half 36 only comprises bristles 21 with lower bristle ends 38, that is to say that all the bristles 21 in the bristle tuft half 36 stand up (at least approximately) to the same height. By contrast with this, in the bristle tuft half 35 there are both bristles 21 with higher bristle ends 37 and bristles 21 with lower bristle ends 38. In the example, the bristles 21 with higher bristle ends 37 are arranged in a contiguous region 39 of the bristle tuft half 35.

Figure 7:
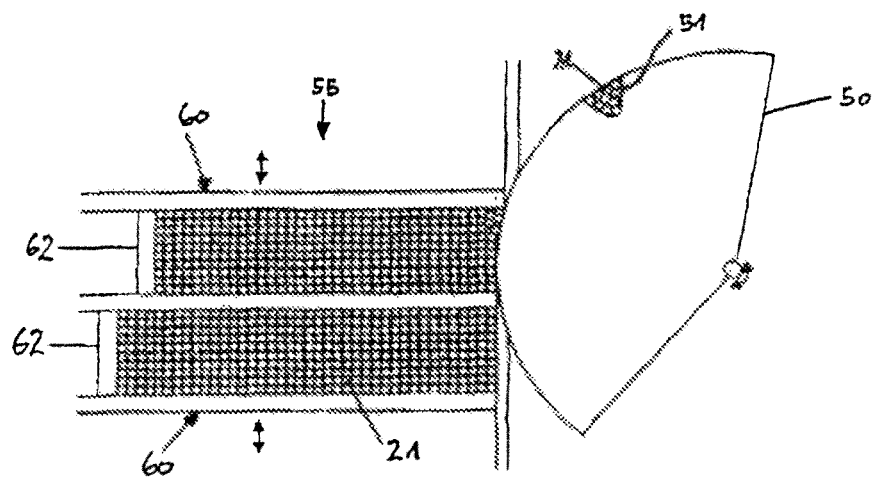
FIG. 7 shows a plan view of a bristle tuft conveyor and a bristle feed with two material channels.

In FIG. 7, a plan view is shown of a bristle tuft conveyor 50 and a bristle feed 55 with two material channels 60 of a tufting machine for toothbrushes (a bristle-providing machine). The bristles 21 are pushed toward the bristle tuft conveyor 50 in the two material channels 60 by pushers 62.

The bristle tuft conveyor 50 is mounted rotatably about an axis about which it performs a forward-backward rotating movement. The extent of the rotation is defined by various points that the notch 51 must run to. On the one hand, this is the reversal point at the end of the material channels 60, on the other hand the point at which the tuft is punched into the blind hole 40 with the anchor 45. When the notch 51 travels along the material channels 60 during the rotation and at this moment is not filled, it fills itself with bristles 21. The removal of bristles 21 at the end of the material channels 60, that is to say at the end opposite from the pusher 62, has the effect that the bristles 21 in the material channel 60 are transported in the direction of the bristle tuft conveyor 50.

The bristles 21 from the different material channels 60 may have different properties, for example different colors. To take the bristles 21 from one or the other material channel 60, the corresponding material channel 60 must move laterally during the phase of the process in which the rearward end of the bristle tuft conveyor closes the material channel 60, in order that the correct material channel 60 is available for filling the notch 51.

Figure 8:
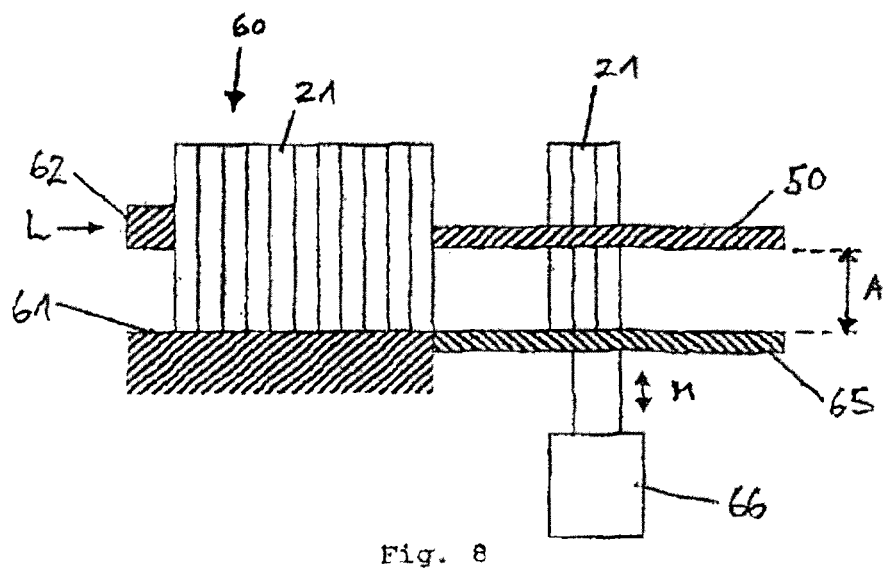
FIG. 8 shows one possible position of an adjustable stop in relation to a bristle tuft conveyor and a material channel.

FIG. 8 shows one possible position of an adjustable stop 65 in relation to a bristle tuft conveyor 50 and a material channel 60. This could be the case, for example, in the upper material channel 60 from FIG. 7.

In FIG. 8, the pusher 62 conveys the bristles 21 in the conveying direction L to the bristle tuft conveyor 50. The stop 65 is arranged such that it can be adjusted by a drive means 66 in its height, i.e. in a direction M perpendicular to the plane of movement of the bristle tuft conveyor 50, or the axis of rotation thereof, or parallel to the bristles 21 in the material channel 60. When bristles 21 are being transported from the material channel 60 to the bristle tuft conveyor 50, in the present case the adjustable stop 65 is positioned at the height of the material channel base 61. As a result, the bristles 21 are guided or supported continuously at at least one of their ends from the material channel 60 until they are removed from the notch 51, in order that they do not fall out of the notch 51 or become stuck in the notch 51. The distance A between the bristle tuft conveyor 50 and the stop 65 is constant. In the position of the stop 65 that is shown, the bristle tuft conveyor 50 is in a first position in relation to the bristles 21 or the length thereof.

Figure 9:
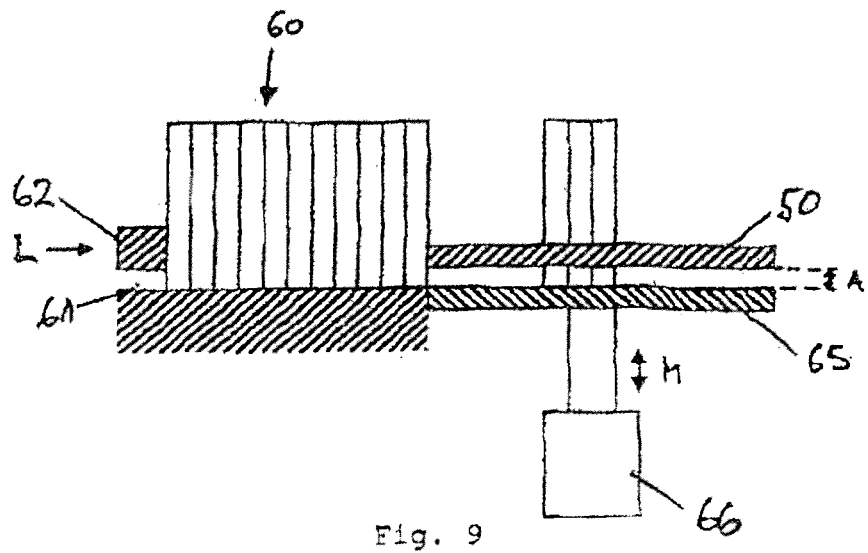
FIG. 9 shows a further possible position of an adjustable stop in relation to a bristle tuft conveyor and a material channel from FIG. 8.

In FIG. 9, the lower material channel 60 from the example from FIG. 7 is represented. The two material channels 60 that are shown in FIGS. 8 and 9, or the corresponding material channel bases 61, are arranged at different levels with respect to the bristle tuft conveyor 50. Each of the arrangements represents an orientation of the higher bristle ends 37 in the finished toothbrush. At the same time, however, the bristle tuft conveyor 50 is always arranged at the same position, it is fixed in terms of its position.

FIG. 9 shows a further possible position of an adjustable stop 65 in relation to a bristle tuft conveyor 50 and a material channel 60. The bristles 21 are in a different position in relation to the bristle tuft conveyor 50 than those shown in FIG. 8. In the position shown of the stop 65, the distance between the stop 65 and the bristle tuft conveyor 50 has been reduced, so that the bristle tuft conveyor 50 or the notch 51 is now no longer located at the same point in relation to the bristles 21 as that shown in FIG. 8.

The bristles 21 are in turn transported in the conveying direction L toward the bristle tuft conveyor 50.

The bristles 21 introduced into the toothbrush head 10 by the devices from FIGS. 8 and 9 have a quite specific orientation with respect to the central longitudinal plane 30. All the bristles 21 introduced by the device shown in FIG. 8 have a specific orientation with respect to the central longitudinal axis 30 of the toothbrush. The bristles 21 introduced by the device shown in FIG. 9 have the opposite orientation. Thus, for example, the bristles 21 of the toothbrush shown in FIG. 1 are dispensed from two such devices. The bristles 21 on the left side of the central longitudinal plane 30 may, for example, be dispensed by the device shown in FIG. 8, those on the right side by the device in FIG. 9. Accordingly, all the tufts of bristles 20 that are dispensed by one device are oriented in the same direction. The arrangements of material channel 60, stop 65 and bristle tuft conveyor 50 in FIGS. 8 and 9 that are respectively described as a single device in this paragraph together form a single device such as that represented for example in FIG. 7. One figure (FIG. 8 or 9) shows the upper material channel 60, the other the lower material channel 60. Which material channel has which configuration is of no relevance for embodying the process according to the invention.

Of central importance for the present invention is the so-called asymmetric punching. This means that the anchor 45 is not introduced centrally with respect to the length of the bristles 21, as is normally the case with tufts of bristles with bristle ends all of the same height.

With respect to the bristle tuft conveyor 50, as it is shown for example in FIGS. 8 and 9, the anchor 45 is introduced directly above it. Since, in the two figures, the bristle tuft conveyor 50 assumes two different positions with respect to the length of the bristles, two different asymmetries are produced. In one case, the ends on one side of the anchor are higher, in the other case the other ends are higher. In FIG. 8, for example, the anchor 45 is introduced closer to the upper end of the bristles 21, that is to say that the bristle ends which touch the material channel base 61 stand up higher. In FIG. 9, the situation is precisely reversed, the bristle ends which touch the material channel base 61 form the lower bristle ends when they have been introduced into the toothbrush head 10.

The adjustable stop 65 is adjustable in direction M between 2 mm and 30 mm, preferably between 4 mm and 10 mm. The surface of the stop 65 is also an important component in the process. To ensure the optimum conveyance of the bristles 21, the surface of the stop 65 is preferably polished or highly polished. If need be, it is also possible to apply to the surface a coating which improves the surface. The aim of the surface treatment or working is to minimize the frictional resistance between the bristles 21 and the stop 65 and in this way achieve good conveyance in a process that is reliable.

The adjustable stop 65 according to the invention from FIGS. 8 and 9 makes it possible in the first place to produce a toothbrush with asymmetrically punched tufts of bristles 20 in a number of orientations or with different distances between the higher and lower bristle ends 37, 38, as explained for example in conjunction with FIG. 1, on a bristle-providing machine with a punching unit (bristle-providing unit). This means that, on account of the adjustable stop according to the invention, advantageously only one anchor-introducing device is necessary.

Figure 10:
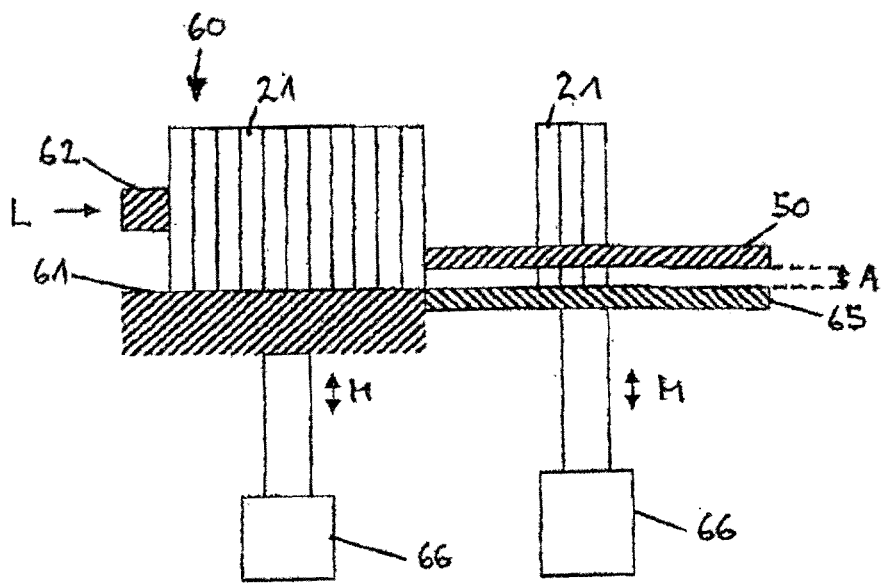
FIG. 10 shows one possible position of an adjustable stop in relation to a bristle tuft conveyor and an adjustable material channel.
Figure 11:
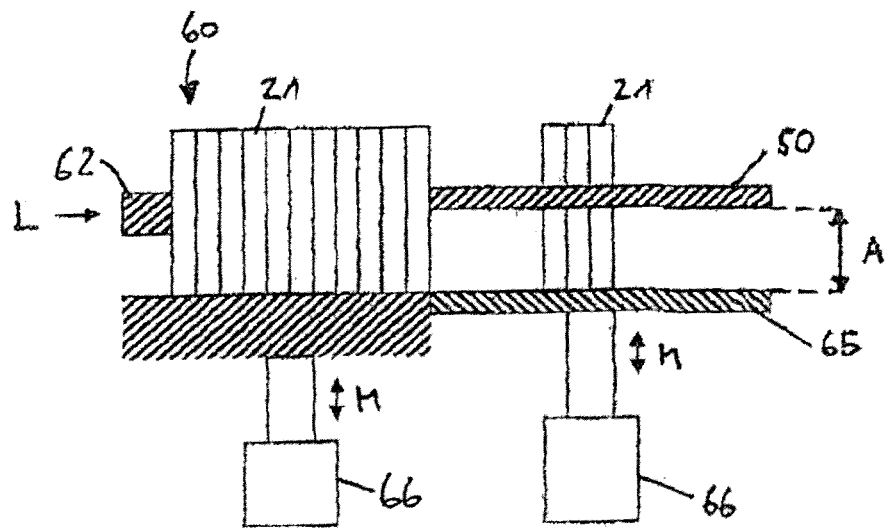
FIG. 11 shows a further possible position of an adjustable stop in relation to a bristle tuft conveyor and an adjustable material channel from FIG. 10.

A further embodiment of the device according to the invention is shown in FIGS. 10 and 11. The fact that both the material channels 60 and the stop 65 can be adjusted in their position in terms of height means that further possibilities of designing the bristle area are obtained. As already in the embodiment shown in FIGS. 8 and 9, the constant in this arrangement is the bristle tuft conveyor 50, which is arranged fixedly in terms of its position. The plan view of the device constructed in this way is the same as in FIG. 7.

FIG. 10 shows one possible position of an adjustable stop 65 in relation to a bristle tuft conveyor 50 and an adjustable material channel 60. As a difference from the devices shown in FIGS. 8 and 9, in this case both the stop 65 and the material channel 60 can be adjusted in their height, by a drive means 66, the material channel likewise being assigned a drive means 66. The direction M in which the height of the stop 65 and/or the material channel 60 is adjustable is at right angles to the plane of movement of the bristle tuft conveyor 50. Pushers 62 transport the bristles 21 in the conveying direction L.

In FIG. 11, a further possible position of an adjustable stop 65 in relation to a bristle tuft conveyor 50 and an adjustable material channel 60 from FIG. 10 is shown. In this case, in turn, both the material channel 60 and the stop 65 are arranged such that they can be adjusted independently of one another by drive means 66 in their height perpendicularly in relation to the plane of movement of the bristle tuft conveyor 50. The stop 65, as well as the material channels 60, are adjustable here in height in the direction M between 2 mm and 30 mm, preferably between 4 mm and 10 mm.

The bristles 21 transported in the conveying direction L by pushers 62 are supported on the one hand by the material channel base 61 and on the other hand by the stop 65, and so are secured against slipping in the perpendicular direction with respect to the conveying direction L. What is special about this arrangement is that the pusher 62 is not adapted in height. It is always kept in the same plane in relation to the material channel base 61, independently of the position of the bristle tuft conveyor 50. Therefore, depending on the how the bristle tuft conveyor 50 is set up in relation to the length of the bristles, i.e. depending on the position of the conveyor, it is necessary to provide additional supporting means at the end of the material channel 60 or above the ends of the bristles, which however do not restrict the functioning of the process. Otherwise, it may be possible for the bristles to be pushed out from the material channel 60 perpendicularly on account of the pressure from the pusher 62.

Furthermore, in the situations shown according to FIGS. 10 and 11, it may be necessary under some circumstances to add a further element which lies above the material channel 60 and prevents the bristles 21 from slipping perpendicularly out of the channel during the movement of the material channel 60 by drive means 66. Whether such an adaptation has to take place depends on the properties of the bristles 21 (surface friction, etc.).

The adjustability of the material channel 60 and of the stop 65 may be variously designed. For example, the two material channels 60 may be adjusted in height by a single drive means 66. Furthermore, however, it is also possible for the material channels 60 to be configured with individual drive means 66 and thus made adjustable independently of each other, which however would necessitate adaptation in the structural design of the arrangement of the material channels. From the aspect of costs, however, the second variant does not bring any major advantages, since the variability of the function does not increase. However, the stop must always be adjustable individually, that is to say independently of the material channels 60, since this is essential according to the invention.

The possibilities of individualization that are produced by the various possibilities for adjustment on the device according to the invention allow brushes with very special bristle patterns to be created. For example, in this way tufts of bristles with different lengths between the higher and lower bristle ends 37, 38 can be achieved on a toothbrush. The drive means 66 may be variously configured. Possibilities for the drive means 66 are, for example, motors (stepping motors, etc.), pneumatic or hydraulic cylinders, or the like. The stop 65 is usually only adjusted when the bristle tuft conveyor 50 is empty, that is to say when no tuft of bristles 20 is being advanced in the notch 51.

It is important that the various means that are used and come into contact with bristles 21, from the material channel 60 until the bristles 21 are introduced into the blind holes, are configured very accurately and the surface thereof has been optimized, for example by being highly polished. As far as the stop is concerned, this has already been described earlier in the text. Consequently, it is additionally achieved that the tufts of bristles 20, or the bristles 21 in the tufts of bristles 20, are introduced into the blind holes 40 in a very accurately aligned manner. This is important since the lower bristle ends 38 are not cut. Therefore, these bristle ends must already have the necessary alignment in relation to one another when they are introduced into the blind hole. Less frictional resistance means in this case fewer displacements of the individual bristles 21.

A further configurational possibility for the process is, for example, to provide the stop 65 shown in FIGS. 8 to 11 with a special form. The stop 65, which in the cases described is of a planar configuration (continuation of the material channel base 61 in a straight line parallel to the bristle tuft conveyor 50), could be designed here as an angled plane (i.e. it has two partial planes arranged at an angle to each other). The plane would in this case be designed such that, after the continuous transition from the material channel base 61, it has an upward or downward slope along the direction of movement of the tuft of bristles in the notch 51. The described distance A would therefore no longer be constant. This could achieve the effect that the asymmetric punching could, for example, be performed more extremely. However, it would be necessary to take special measures in order for this to be possible for both directions of orientation of the tufts of bristles 20 in the toothbrush head 10—since the bristle ends which lie against the stop 65 during the conveyance are in one case the higher bristle ends 37 and in the other case the lower bristle ends 38 in the finished toothbrush. Possible measures here would be, for example, that, in addition to the movement in height along the direction of movement M, the stop 65 also moves in another direction, and in this way a different profile is obtained in the movement curve of the tuft of bristles in the notch 51 on the stop.

Furthermore, it is also possible for the driven stop 65 to be adjusted during the conveying of a tuft of bristles. In this case, the adjustment of the height with respect to the bristle tuft conveyor 50 would be possible in both directions and the different arrangements of the higher and lower bristle ends 37, 38 could thereby be served.

To create toothbrushes with tufts of bristles 20 of different sizes, a bristle tuft conveyor 50 in which a variable notch 51 is made could be used in the process. A variable notch 51 could be adapted in its size during the process, when it is not filled, so that ultimately a greater or lesser number of bristles 21 are transported out of the material channel 60 into the blind holes 40.

The configuration of the toothbrush and the orientation of the higher and lower bristle ends 37, 38 are significant for the efficiency of the process and also for the cycle time of providing the toothbrush with bristles. The orientation of the tufts of bristles is preferably fixed such that, in the bristle-providing process, a number of tufts of the same orientation can always be introduced into the head part 10. As a result, the stop 65 and the material channels 60 do not have to be changed over after every tuft of bristles. The process becomes quicker and also less susceptible to faults.

In the process of providing the toothbrushes with bristles, after they have been fastened in the head part 10, the bristles 21 are reworked. This means that they are, inter alia, profiled. The surface profile is achieved, for example, by cutting away or milling away the parts of the bristles that are too long. Furthermore, they are subsequently rounded.

The further following profiling steps have likewise been further developed and supplement the invention. This is explained in detail in conjunction with FIG. 12. So-called displacement rails 70, which partially displace the bristles 21 of the toothbrush so as to make the bristles 21 to be worked better accessible, are used in the working steps for the profiling of the toothbrushes. According to the invention, in a first step, tufts of bristles 20 are profiled at their higher bristle ends 37. A profiling of the bristle tuft half 36, which consists only of lower bristle ends 38, is preferably not performed. Otherwise, a corresponding displacement of the higher bristle ends 37 would be necessary.

Figure 12:
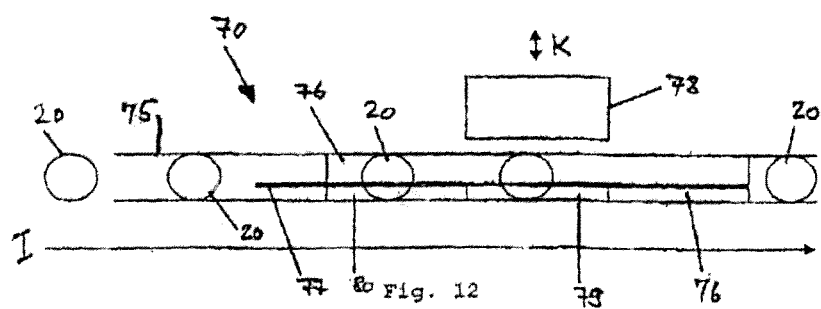
FIG. 12 shows a segment of a displacement rail of the device.

FIG. 12 shows a segment of a displacement rail 70 of the device for providing toothbrushes with bristles. A single tuft of bristles 20 is introduced into a bristle tuft channel 75 in direction of movement I. The bristle tuft channel 75 runs parallel to the direction of movement I and the tufts of bristles 20 are advanced in the direction of movement. As this happens, an edge 77 arranged parallel to the longitudinal direction of the tuft of bristles 20 reaches into the tuft of bristles 20 and divides it into two parts. The two parts are not of the same size. The larger part of the tuft of bristles 20 is then led through a displacement channel 76. As this happens, the free bristle ends are displaced, that is to say deflected and no longer stand up while they are led through the channel. In terms of the cross section, the displacement channel 76 is formed in this region similar to a U profile or V profile, that is to say it is closed on three sides and can in this way receive the bristles 21.

After the division of the tuft of bristles 20, the less large part of the tuft of bristles 20 is likewise displaced by the edge 77 in a first part and led into an ordering channel 80, but subsequently released again right away as it runs through. The release takes place in a releasing region 79 as the tuft of bristles 20 is being led through the bristle tuft channel 75. In this releasing region 79, the bristles 21 of the tuft of bristles 20 are not displaced, so that the free bristle ends stand up substantially perpendicularly and are shortened to the desired length by a cutting knife 78 or some other working means, for example a milling cutter, which moves back and forth at right angles to the direction of movement I of the tuft of bristles 20 along the direction of movement K of the cutting knife. Subsequently, the bristles 21 not displaced are in turn led into a displacement channel 76', before they are released again. This displacement of the worked bristles 21 has no processing reasons. The displacement is preferably included, however, to stabilize the edge 77. This achieves the effect that the edge 77 vibrates less during the working, or is (temporarily) bent less as a result of the loading, which makes working more difficult, or that the dividing of the tufts no longer takes place constantly, since the reaching of the edge 77 into the tuft of bristles 20 varies.

A complete displacement rail 70 is an arrangement in series of a number of segments according to FIG. 12, preferably two such segments being arranged in series with one another. The difference between the two segments following one after the other may be that the edge 77 is positioned differently in relation to the tuft of bristles 20, and so can be displaced differently. Moreover, the displacement channel 76 may be arranged on the other side of the bristle tuft channel 75 in the longitudinal direction.

For the production of tufts of bristles 21 according to FIGS. 1-3, the displacement channel is required in the first part by analogy with the variant shown in FIG. 12 and in the second part almost in mirror image. This means that the edge 77 is provided such that the smaller part comes to lie on the upper side (see FIG. 12). In addition, the displacement channel 76 is provided on the other side in the longitudinal direction of the bristle tuft channel 75. The ratios of the division of the tufts of bristles 20 by the edge 77 are the same in both steps, just differently oriented or mirror-inverted.

Figure 13:
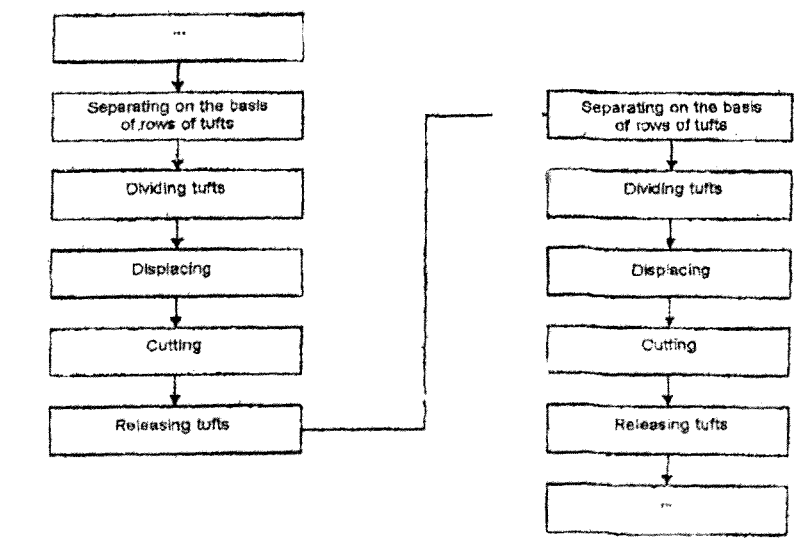
FIG. 13 shows a sequence as carried out by the displacement rail shown in FIG. 12.

In FIG. 13, a sequence such as that carried out with the displacement rail shown in FIG. 12 is shown in its individual successive steps. In a first step, the tufts of bristles 20 arranged in series are separated by introduction into the bristle tuft channel 75. Subsequently, each individual tuft of bristles 20 is divided into two parts, the larger part of the divided tuft of bristles 20 being displaced, and therefore not accessible to the cutting knife 78.

For the creation of tufts of bristles 20 according to FIGS. 1-3, the larger, displaced part of the tuft of bristles 20 comprises approximately two thirds of the bristles 21 of the tuft of bristles; generally, the displaced part of the tuft of bristles 20 comprises between 55% and 85%, preferably between 55% and 70%, of the bristles 21. The smaller, not-displaced, part of the tuft of bristles 20 comprises in the case of FIGS. 1-2 approximately one third of the bristles 21 of the tuft of bristles 20. In a next step, the part of the tuft of bristles 20 that is not displaced, and therefore is standing up, is cut to the desired length. After the cutting operation, the tuft of bristles 20 is released again. This means that the displaced part is led out from the displacement channel 76. Once the tuft of bristles 20 has been released, the entire operation is repeated, so that each tuft of bristles 20 is cut twice. In this case, different parts of the tuft of bristles 20 are respectively displaced in the two operations, certain regions being displaced, and accordingly not cut, in both operations.

With regard to the displacement, it is the case that the division of the bristles 21 by the edge 77 is in the range of very small dimensions. Moreover, the form in which the bristles 21 protrude from the blind hole 40 is to a certain extent random. It is therefore not possible to define accurately how many bristles 21 are, for example, displaced or how many bristles 21 have higher bristle ends 37 in the later, worked case. The numbers always vary within certain ranges.

For the actual realization of toothbrushes with transverse rows according to FIG. 1, this means that the toothbrush is oriented such that the longitudinal axis 29 of the toothbrush is arranged perpendicularly in relation to the direction of movement I.

A number of bristle tuft channels 75 are arranged directly next to one another, so that a toothbrush comprising a multiplicity of rows, or the tufts of bristles 20 thereof, are worked at least partially in parallel.

If toothbrushes with rows which are arranged at an angle deviating from 90° in relation to the longitudinal axis 29 of the toothbrush are created, the brush must be introduced into the displacement rail 70 in a differently oriented manner for the working. In order that the processing is possible, the longitudinal axis 29 of the toothbrush is arranged in terms of the angle such that the direction of the rows is parallel to the direction of movement I, i.e. the direction of the bristle tuft channels 75.

It is important in the case of such toothbrushes that all the tufts of bristles 20 that are to be worked into tufts of bristles 20 with higher and lower bristle ends are arranged in transverse rows which do not overlap. The symmetries are in this case achieved with respect to an axis provided at an angle to the longitudinal axis 29.

To illustrate still further the representation of the segment of the displacement rail 70 in FIG. 12 and the comparison with the tuft of bristles 20 according to FIG. 6 and the corresponding working steps, the following should be noted: the tuft of bristles shown in FIG. 6 is introduced into the bristle tuft channel 75 perpendicularly in relation to the anchor 45. For this tuft of bristles 20, the direction of movement I is accordingly likewise perpendicular to the anchor 45.

In the example now presented, the direction of movement is fixed such that the bristle tuft half 35 with the higher bristle ends 37 runs in front. This means that firstly the entire tuft of bristles 20 is introduced into the bristle tuft channel 75. Subsequently, the edge 77 divides the tuft of bristles 20 along the later transition from the higher bristle ends 37 to the lower bristle ends 38. The bristle ends 37 that will later stand up higher together with the bristle ends 38 that will later stand up lower on the left side of the tuft 20 are displaced. After that, the lower bristle ends 38 on the right side of the tuft of bristles 20 are cut to their length. In actual fact this means that the corresponding segment between the anchor 45 and the higher bristle ends 37 is cut away. After that, the tuft of bristles 20 is released again and, in the second step, the working takes place on the left side of the tuft of bristles 20.

In the course of the profiling of the tuft of bristles 20, in addition to the thinning out, it is also possible to profile the higher and lower bristle ends 37, 38. This either takes place before the thinning out just described or thereafter; this profiling preferably takes place after the thinning out. The higher bristle ends 37 may, for example, be cut such that they form a desired profile. For example, an area, for example of a flat (planar) or undulating form. Other forms are likewise conceivable. For the finished toothbrush, this may have the end effect in terms of the configuration that, for example, different lengths between the higher and lower bristle ends 37, 38 are achieved within the same bristle area.

Furthermore, for example, the higher bristle ends 37 may be displaced and the lower bristle ends 38 in the bristle tuft half 36 cut in this way. However, this step is preferably not carried out and is achieved by a very precise and well-aligned introduction of the bristles 21 into the blind holes 40.

In the process sequence, after the profiling and thinning out of the tufts of bristles 20, the process of rounding the bristles 21 takes place. When cylindrical bristles 21 are used, all the bristle ends 37, 38 are rounded. When bristles that are pointed at one end are used, the higher bristle ends 37 being pointed, the cylindrical ends, that is to say the lower bristle ends 38, are rounded. When bristles pointed at both ends are used, either no profiling and no rounding takes place, or a profiling takes place and only the lower bristle ends 38 are rounded. Accordingly, the tips of the lower bristle ends 38 are also to a certain extent rounded.

In a first step, or in a first sequence of steps, the lower bristle ends 38 are thereby rounded. This means that the grinding device that is used for the rounding is set to the height of these bristle ends 38, and the higher bristle ends 37 are preferably not displaced thereby. One or more grinding wheels arranged one after the other in the process then perform the rounding. Subsequently, in a second step, or in a second sequence of steps, the rounding of the higher bristle ends 37 takes place. For this purpose, the grinding device is set to the height of these bristle ends 37. In turn, one or more grinding wheels arranged one after the other perform the rounding. After that, the functional part of the toothbrush is complete.

One special aspect of the rounding process is that one or more grinding wheels are used for each rounding height. In this case, the same number or more grinding wheels are used for the second rounding step than for the first step. This may be necessary because the first rounding could cause certain damaging effects to the higher bristle ends 37. Therefore, these bristle ends 37 must tend to be rounded longer than the lower bristle ends 38 rounded in the first step.

Further possibilities for configuring the rounding process are possible to minimize any damaging effects on the higher bristle ends 37 during the first rounding step. For example, the higher bristle ends 37 could be displaced during the first rounding step.

For the realization of toothbrushes according to the invention and toothbrushes produced according to the invention, a wide variety of types of bristle can be used. With preference, cylindrical bristles 22 or pointed bristles 23 are used.

Figure 14A:
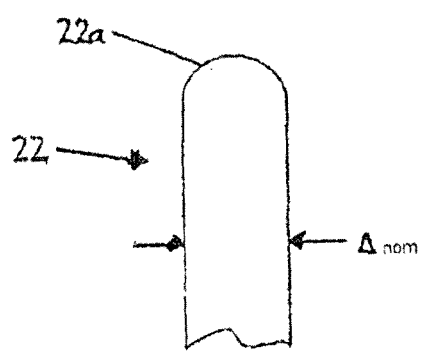
FIG. 14 shows the form of the end region of a cylindrical rounded-off bristle (FIG. 14a) and of a cylindrical pointed bristle (FIG. 14b)

FIG. 14*a* shows the bristle end of a cylindrical bristle 22. The cylindrical bristles 22 are preferably produced from polyamide (PA). They have a substantially constant nominal diameter $\Delta_{nom}$ over the length of the bristles. The nominal diameter is the diameter at the thickest point of the bristle. The nominal diameter is, for example, 0.15 to 0.25 mm. The tip 22*a* of the bristle 22 is rounded off in the end state in the toothbrush.

Figure 14B:
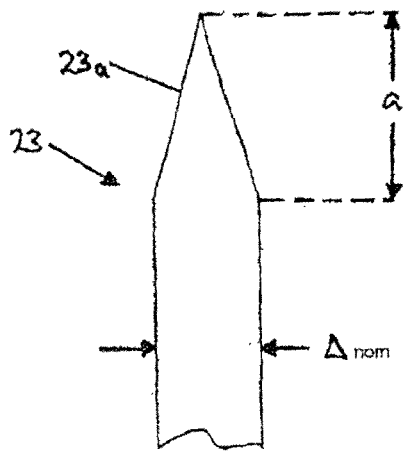
Figure 15:
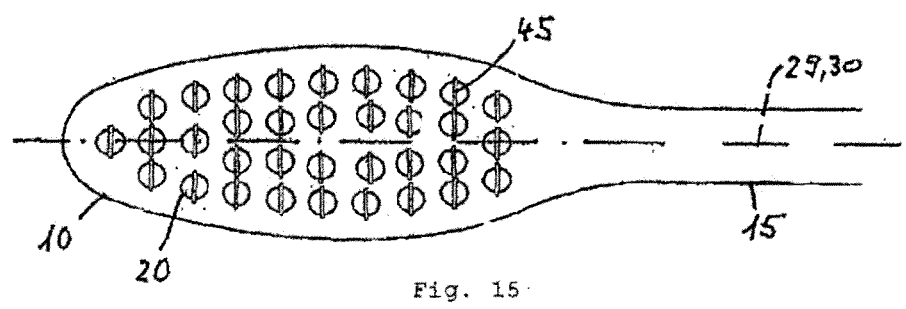
FIG. 15 shows a further possible arrangement of the anchor in a bristle area on a toothbrush, in plan view.
Figure 16:
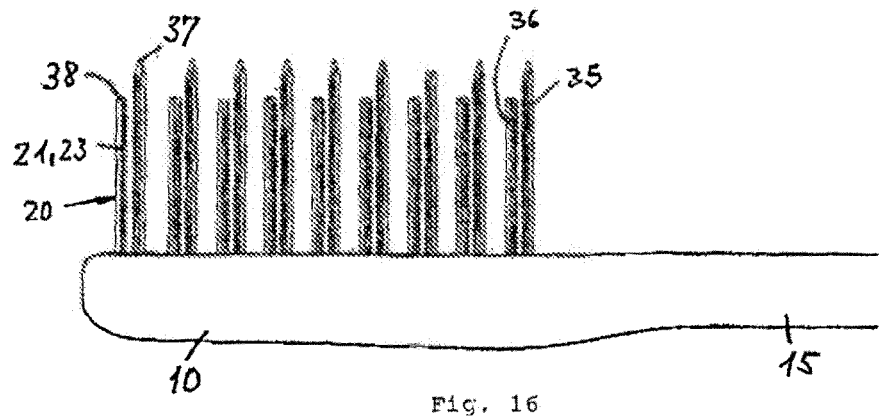
FIG. 16 shows a variant of the provision of bristles, with the anchor positions shown in FIG. 15, in side view.

Pointed bristles 23 are presented in FIG. 14*b*. Pointed bristles 23 are preferably produced from polyester (PBT) and likewise have a constant diameter, for example likewise a nominal diameter of 0.15-0.25 mm, over a region of their length. The bristle 23 tapers toward the tip 23*a*, beginning at a distance a measured from the tip 23*a*. Measured from the tip 23*a*, the diameter at the corresponding point corresponds, for example, to the following values:

| Distance | % of the nominal diameter | |
|---|---|---|
| (mm) | Mean value | Tolerance range |
| 0.1 | 8% | 5-15% |
| 1 | 25% | 15-35% |
| 2 | 45% | 30-60% |
| 3 | 60% | 50-80% |
| 4 | 75% | 60-90% |
| 5 | 80% | 70-90% |
| 6 | 85% | >75% |
| 7 | 90% | >80% |

The pointing process is based on reduction of the diameter by means of a chemical process. Depending on the length of time during which the bristle is left in the chemical substance, the plastic disintegrates and the diameter is reduced. The form of the tip can be influenced in this way.

In principle, two types of pointed bristles 23 exist. Those which have a point only at one end and those which have a point at both ends of the bristle. As far as the dimensions are concerned, the pointing is designed in both cases in the way specified above. The bristles 23 that are pointed at one end have a point at one end, and at the other end are cylindrically designed and may be rounded off. The bristles 23 pointed at both ends are configured with a point at both ends.

To ensure sufficient stability of the individual filaments, the nominal diameter is left over a large part of the length at over 75%. The table given above shows that the pointing of the filaments takes place predominantly over the last 4 to 5 mm. With this configuration, the tip 23a can optimally reach minute fissures and the interdental spaces while having sufficient stability of the filament.

To achieve sufficient flexibility of the filaments, a length, from leaving the blind hole 40 of the head part 10, of between 7 and 13 mm is chosen for all types of bristle.

In the case of toothbrushes according to the invention, the bristles 21 may be completely or partially colored. Accordingly, in the case of partially colored bristles 21, for example, only the bristle ends or only one bristle end or else everything with the exception of the bristle ends may be colored. The coloration itself may be designed as an indicator coloration or as a permanent coloration. In the case of the indicator coloration, the color is worn away during the course of use, and thus serves as an indicator of use.

The cylindrical bristles 22, which are produced from polyamide, may for example be colored with food dyes and be provided with a coating over the dye. Possible food dyes that can be used by, for example, are for blue "Aluminum Lake of 3,3'-dioxo-2,2'-diindolinyidene-5,5'-disulfonic acid", for yellow "Aluminum Lake of 5-hydroxy-1-(4-sulfophenyl)-4-(4-sulfophenylazo)-3-pyrazolecarboxylic acid" or "Aluminum Lake of 6-hydroxy-5-(4-sulfophenylazo)-2-naphthalene sulfonic acid". These dyes are designed to be suitable for food contact.

Once the dyes have been applied to bristles 21, the surface is usually no longer of such a quality that allows automatic processing on toothbrush bristle-providing machines. Therefore, the entire bristles, or at least the colored portions of the bristles, are provided with a coating. This coating makes the surface smoother, and so in turn makes automatic processing possible.

Pointed bristles 23, which are produced from polyester, cannot be colored in this way. The coloration of these bristles 23 must take place by a chemical process, which however will not be discussed in detail at this point. The process is known per se.

The advantage of coloration may be that the technical aspect of the bristles of different lengths can be made visible, for example if only the higher bristle ends 37 are colored, or if only the lower bristle ends 38 are colored. Furthermore, the design as an indicator portion can create the benefit for the customer of an indication of use.

With preference, the part of the bristles 21 that comprises the higher bristle ends 37 is colored. The coloration of both ends is likewise possible.

If it only concerns the tips of the bristles, the coloration has on the finished toothbrush a length of 2 mm to 10 mm, preferably between 3 mm and 8 mm. On account of the processing, the coloration is longer, or adapted, on the bristles that have not been processed, since otherwise some parts of the coloration are ground away or cut away. Accordingly, the coloration in the raw material does not have to be of the same length at both ends of the bristles, just as it can also vary in the end product. With preference, the coloration in the end product is nevertheless of the same length at both ends of the bristle if both ends of the bristle are colored.

Furthermore, instead of bristles which have been extruded from a single material, it is possible to use bristles which are co-extruded, i.e. bristles which have been extruded from two or more materials. These bristles have an outside diameter of from 0.1 mm to 0.4 mm, preferably from 0.1 mm to 0.25 mm. However, the construction is such that they consist of a core and a shell. The core has a diameter of from 0.8 mm to 0.16 mm, preferably 0.1 mm to 0.14 mm. The shell around the core has a thickness of from 0.02 mm to 0.08 mm, preferably 0.03 mm to 0.05 mm. The core and the shell preferably consist of polyester. However, two different materials may also be used. The core and the shell are preferably not of the same color. It is therefore possible by chemical or mechanical pointing of the bristles to create the same effect as can be achieved in the case of bristles with colored tips. The pointing involves at least partially removing the shell, and in this way the core becomes visible from the outside. The rounding of these same bristles produces a similar effect, only that in this case the end of the bristles is rounded and not pointed. In this case, the rounding involves removing part of the shell and exposing the core to view. The exposing of the core in rounding is much less than in pointing.

In FIGS. 15 to 18, a further configurational variant of the invention is shown. The anchors 45 are introduced into the head part 10 at an angle of 90° or 90°+/−20°, preferably 90°+/−10°, with respect to the longitudinal axis 29.

Figure 19:
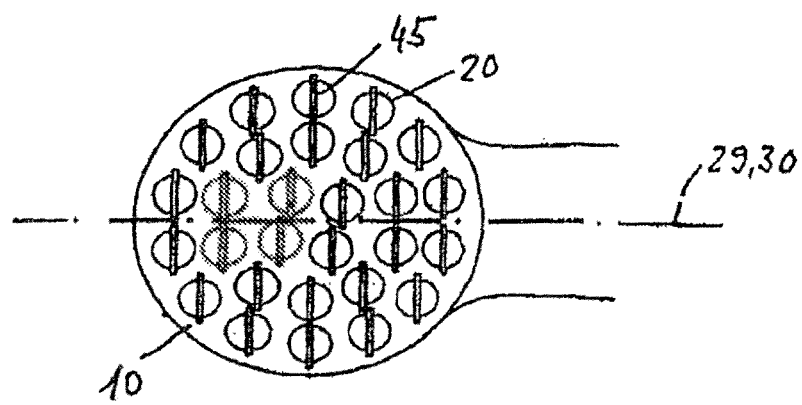
FIG. 19 shows a further possible arrangement of the anchors in a bristle area of an electrically operated toothbrush with rotating or oscillating motion, in plan view.
Figure 20:
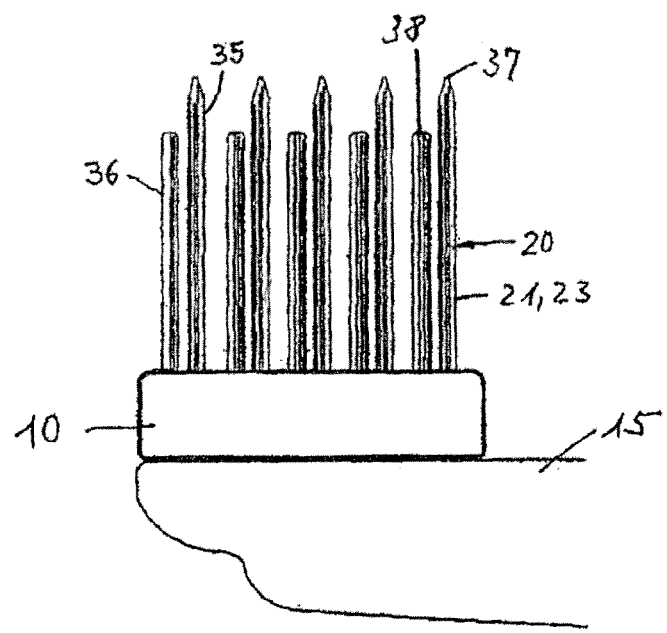
FIG. 20 shows a further variant of the provision of bristles, with the anchor positions shown in FIG. 19, in side view.
Figure 21:
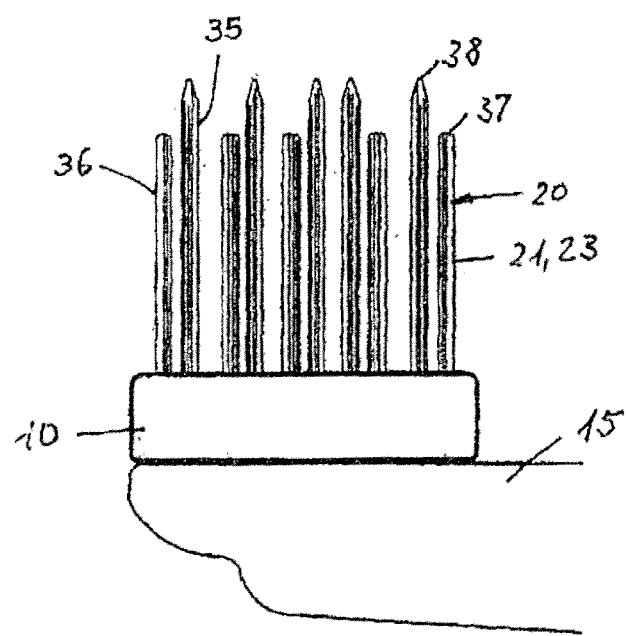
FIG. 21 shows a further variant of the provision of bristles, with the anchor positions shown in FIG. 19, in side view.

In FIGS. 19 to 21, the same is shown on a round head part 10 for an electric toothbrush with rotating or oscillating motion. In this case, the longitudinal axis 29 of the toothbrush lies substantially at right angles to the anchors 45 represented.

The tufts of bristles 20 shown in the figures have in turn higher bristle ends 37 and lower bristle ends 38. Preferably, bristles 23 that are pointed at one end are used. The higher bristle ends 37 are in this case formed by pointed ends of the bristles 21, which is graphically represented in FIGS. 16 to 18 and 20 and 21 by the pointed end of the tufts.

The tufts of bristles 20 may be constructed differently with respect to the orientation of their higher and lower bristle ends 37, 38. In this case it is possible for the tufts of bristles 20 to be uniformly oriented, as shown for example in FIGS. 16, 18 and 20. This means that the bristle tuft halves 35 with the higher bristle ends 37 are always arranged on the same side of the anchor 45, for example always come to lie against the handle of the toothbrush body or are always directed away from it.

Figure 17:
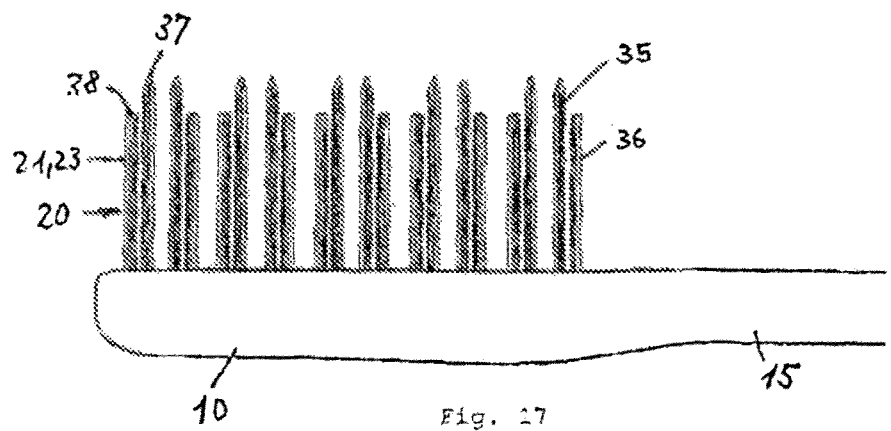
FIG. 17 shows a further variant of the provision of bristles, with the anchor positions shown in FIG. 15, in side view.
Figure 18:
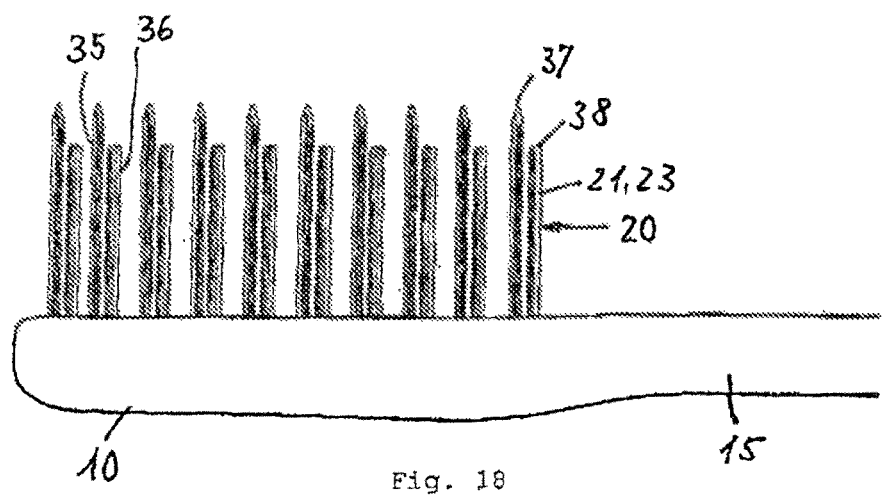
FIG. 18 shows a further variant of the provision of bristles, with the anchor positions shown in FIG. 15, in side view.

FIG. 17 shows the opposite arrangement of the tufts of bristles 20. The higher bristle ends 37 or the relevant bristle tuft halves 35 and also the lower bristle ends 38 or the relevant bristle tuft halves 36 of the various tufts of bristles 20 are always directed toward one another. As a result, a better interdental effect is achieved during use of the toothbrush than in the case of the uniform alignment of the higher bristle ends 37 in the tufts of bristles 20. The clusters penetrate better into the interdental spaces, because they are surrounded by larger areas with lower bristle ends 38. This arrangement is also possible in the case of brush heads such as those shown in FIGS. 20 and 21.

FIG. 21 shows the arrangement in which some of the tufts of bristles 20 are oriented to one side and others to the other side. This configurational variant—arrangement variant—may likewise be realized on elongate head parts 10.

The higher and lower bristle ends 37, 38 are arranged identically with respect to the anchor 45, as shown in FIG. 2. However, the embodiments shown in FIGS. 15 to 21 are designed such that preferably no reworking of the bristles is necessary any longer after the anchors have been introduced. There is preferably no reduction in the number of higher bristle ends 37.

Preferably, no rounding of the lower bristle ends 38 takes place either, because bristles 23 that are pointed at one end and are already rounded at the end of the bristle 23 opposite from the pointing before they are introduced into the brush body are preferably used. The length ratios in tufts of bristles 20 with bristles 23 that are pointed at one end correspond to those ratios that have been described for the cylindrical bristles 23.

For the production of toothbrushes with tufts of bristles according to the brush heads in FIGS. 15 to 22, a device such as that shown in FIGS. 7 to 11 is used, with the difference that neither the stop 65 nor the material channel 60 can or must be adjusted in height during the process. In the material channel 60, the bristles 23 that are pointed at one end are arranged such that the rounded end rests on the material channel base 61 and the pointed ends point away from the material channel base 61. This arrangement achieves a better quality of the alignment of the bristles 23 in the tufts of bristles 20, since the tufts of bristles 20 are in this case not reworked.

If the pointed ends were to lie on the material channel base 61, not all the bristles 23 would stand up to the same extent, since several bristles 23 would buckle, since the cross section decreases in the region 23a of the pointing. This would have the effect that the alignment would become poorer. In order that different alignments of the higher and lower bristle ends 37, 38 can nevertheless be achieved during application, the head part 10 is turned in the working process. This means that the bristles 23 are always brought into the same orientation and just the head part is varied in its orientation, and in this way the orientation of the tufts of bristles 20 in the finished toothbrush does not have to be uniform.

Figure 22:
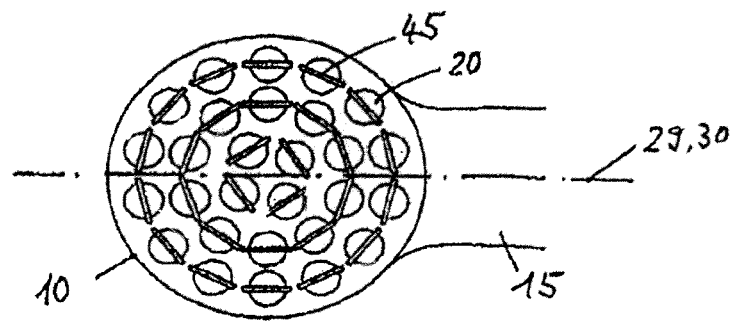
FIG. 22 shows a further possible arrangement of the anchors in a bristle area of an electrically operated toothbrush with rotating or oscillating motion, in plan view.

In FIG. 22, a head part 10 for an electric toothbrush with rotating or oscillating motion is shown. The anchors 45 are in this case arranged at an angle of 90° or 90°+/−20°, preferably 90°+/−10°, with most preference 90°, in relation to the radius of the head part 10. They lie at a tangent to the circles formed by the center points of the tufts of bristles 20.

The tufts of bristles 20 shown in the figures have in turn higher bristle ends 37 and lower bristle ends 38. Bristles 23 that are pointed at one end are preferably used. The higher bristle ends 37 are in this case formed by pointed ends of the bristles 23.

In this arrangement of the anchors 45, all the tufts of bristles 20 may be oriented identically, for example such that the higher bristle ends 37 of each tuft of bristles 20 are directed toward the center point of the bristle area or else such that they are directed away from it.

Furthermore, the tufts of bristles 20 may also have a uniform orientation of the higher and lower bristle ends 37, 38 in the manner of a circle, for example in the configuration that the higher and lower bristle ends 37, 38 of different tufts of bristles 20 are respectively oriented toward one another. Furthermore, it is also possible for the tufts of bristles 20 to be oriented alternately on the circles.

A further configurational variant of the tangential arrangement of the anchors 45 is that, in the bristle area with a round or elongated extent, not all the tufts of bristles 20 have anchors 45 in the alignment mentioned. This is for example so that certain anchors are nevertheless oriented at right angles to the longitudinal axis 29, or have a different orientation.

It is also possible to design a bristle area in which some of the bristle holes are created in a circular arrangement, but others are configured in rows parallel to the longitudinal direction. Here once again, the anchor alignment is not uniform over the entire bristle area.

Figure 23:
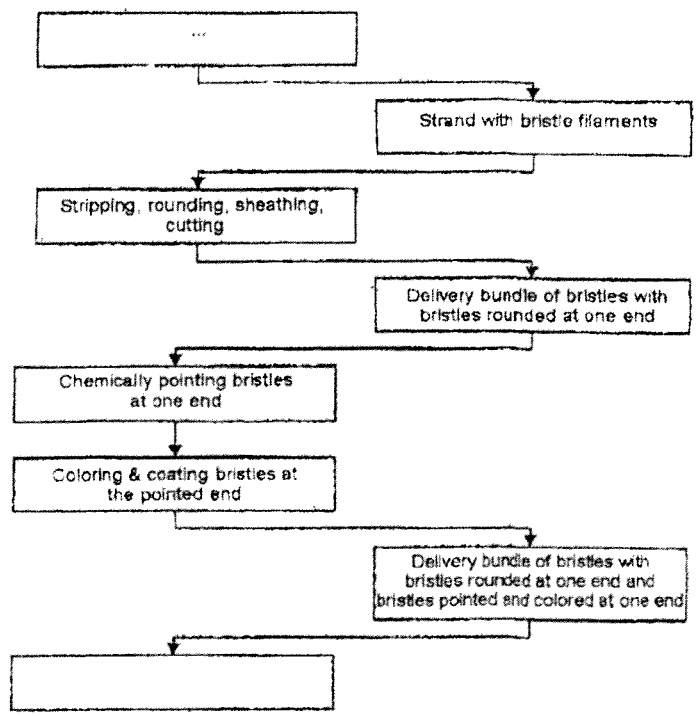
FIG. 23 shows the process sequence for producing bristles that are pointed and colored at one end, with a rounded cylindrical bristle end.

A sequence explaining how the production of bristles 23 that are pointed at one end and have a rounded-off opposite end and coloration of the pointing takes place is described in conjunction with FIG. 23.

The bristle filaments are introduced into the process on the bristle strand. In this case, a multiplicity of filaments are bundled by means of a sheath and have a length which is a multiple of the final length of the bristles in the toothbrush. The length may, for example, lie in the range from 80 cm to 120 cm. On the one hand the sheath serves here for the bundling of the filaments, in order that they remain lying against one another, and on the other hand the sheath has a protective function, that the filaments are soiled or damaged less.

In a first step, these strands with bristle filaments are prepared for the working operation. This may, for example, comprise at least partially stripping back the sheath and clamping them in the device in a way corresponding to the subsequent working.

The working step comprises, for example, the rounding of the free end of the bristle strand. In this case, all the bristle ends of the bristle strand of are rounded with one another. The grinding element, for example a diamond grinder, rounds all the bristle ends of the bristle strands in one step.

Since the bristle strand has been at least partially freed of the sheath in the previous step, the bristle filaments can move out of line during the rounding process. An individual movement of the filaments is allowed to a limited extent. The rounding is better and more regular as a result.

After that, the bristle strand is sheathed again, i.e. provided with a sheath, and is subsequently cut to the size of a delivery bundle of bristles. These two steps may also happen in the reverse sequence. The delivery bundle of bristles is in this case a piece of the bristle strand of a length that corresponds approximately to more than double the bristle length.

Once the bristles have then been rounded at one end, the working of the other end of the bristles follows. This end is pointed and, if need, be colored. The pointing takes place in a first step and is performed by chemical means; the chemicals undertake the removal of material. After that, the pointed ends are colored; possible parameters and properties of the coloration have already been mentioned above, and provided with a coating. The coating serves the purpose of making the nature of the surface (frictional values, etc.) of the individual bristles such that they can be processed by machine.

Subsequently, the bristles that are pointed at one end are packed in delivery bundles of bristles (which then have a different appearance than the delivery bundles of bristles before). In this case, the tips of all the bristles point in the same direction and the delivery bundles of bristles have a diameter of, for example, 3 to 5 cm. The form of the delivery bundles of bristles is preferably of an elliptical to rectangular configuration, on account of their transporting medium, for example an elongate cardboard packaging.

The length of the delivery bundles of bristles is from 40 mm to 60 mm, preferably from 45 mm to 55 mm, with a width of from 25 mm to 40 mm, preferably from 30 mm to 35 mm. In this configuration/delivery form, the width of the delivery bundle of bristles corresponds substantially to the width of the material channel 60, cf. FIG. 7. This allows easier introduction of the delivery bundles of bristles into the material channel 60, without the fragile delivery bundles of bristles having to be deformed too much. Furthermore, in this form, the delivery bundles of bristles can be transported in an easier and more space-saving manner in an elongate cardboard packaging. Furthermore, the delivery bundles of bristles have laterally around the bundle a retaining strip of limited length, which holds the large number of pointed bristles together. On account of the limited length of the retaining strip, virtually no pressure is exerted on the pointed bristles in the delivery bundle of bristles.

For the production of toothbrushes according to the invention, various plastics may be used. Possibilities from the area of thermoplastics are, by way of example:

styrene polymers such as styrene acrylonitrile (SEN), polystyrene (PS), acrylonitrile butadiene styrene (ABS), styrene methyl methacrylates (SMMA), styrene butadiene (SB, for example BDS K-Resin from the Chevron Phillips Chemical Company);

polyolefins such as polypropylene (PP), polyethylene (PE), for example also in the forms of high-density polyethylene (HDPE) or low-density polyethylene (LDPE);

polyesters such as polyethylene terephthalate (PET) in the form of acid-modified polyethylene terephthalate (PETA) or glycol-modified polyethylene terephthalate (PETG), such as GN005 or 6763 from the Eastman Chemical Company, polybutylene terephthalate (PBT), acid-modified poly(cyclohexanedimethanol terephthalate) (PCT-A), such as BR003 from the Eastman Chemical Company, glycol-modified poly(cyclohexanedimethanol terephthalate) (PCT-G), such as DN004 from the Eastman Chemical Company;

cellulose derivatives such as cellulose acetate (CA), cellulose acetobutyrate (CAB), cellulose propionate (CP), cellulose acetate phthalate (CAP), cellulose butyrate (CB);

polyamides (PA), such as PA 6.6, PA 6.10, PA 6.12;

polymethylmethacrylate (PMMA);

polycarbonate (PC);

polyoxymethylene (POM);

polyvinyl chloride (PVC); and polyurethane (PUR).

Examples from the area of thermoplastic elastomers (TPEs) are:

thermoplastic polyurethane elastomers (TPE-U);

thermoplastic styrene elastomers (TPE-S), such as for example a styrene-ethylene-butylene-styrene copolymer (SEBS) or styrene-butadiene-styrene copolymer (SBS);

thermoplastic polyamide elastomers (TPE-A), such as for example Grilflex® from EMS Chemie AG;

thermoplastic polyolefin elastomers (TPE-O); and thermoplastic polyester elastomers (TPE-E).

In the case of a non-transparent brush, PP is used with preference as the hard component, with most preference PP with a modulus of elasticity of 1000-2400 N/mm2, preferably 1300 to 1800 N/mm2. For a brush of a transparent design, polyesters are used with preference as the hard component, such as the cited BR003, CAP, PA, PMMA, SAN or ABS.

A TPE-S is used with preference as the soft component. The Shore A hardnesses of the soft plastic preferably lie below 90 Shore A. The soft component may be integrated both as a component on the handle body of the toothbrush and as a massaging or cleaning element in the toothbrush head 10.

The construction of the bristle area is in principle possible with great variability. Cylindrical bristles 21, 22, 23 that are pointed at one end and at both ends may be combined in any desired way in the bristle area. The tufts of bristles 20 may be directly integrated and combined in any desired number as tufts of bristles 20 with higher and lower bristle ends; also possible, in addition, are the conventional forms of tufts of bristles, in which all the bristles in the tuft stand up to the same height. Furthermore, soft-elastic massaging and/or cleaning elements may be combined in the head part 10 in any desired arrangement with the aforementioned types of bristle and types of tuft.

The tufts of bristles 20 with higher and lower bristle ends 37, 38 may, for example, be arranged alternating with conventional tufts of bristles in the form of transverse rows, it being possible for the conventional tufts of bristles to have their bristle ends lying lower than the higher bristle ends 38. The tufts of bristles 20 with higher and lower bristle ends 37, 38 may form closed contours around other tufts of bristles or else around soft-elastic massaging and/or cleaning elements. For example, they may be arranged such that they surround the bristle area.

One special configurational variant of tufts of bristles 20 with higher and lower bristle ends 37, 38 is the arrangement of these tufts of bristles 20 at an angle deviating from 90° with respect to the head part 10. This means that slanting tufts of bristles 20 are formed, which may also cross and in this way make X-shaped arrangements possible. These are possible longitudinally and transversely on the brush head. For example, a toothbrush head 10 may be designed as having on it transverse rows in which all the tufts of bristles 20 are inclined in the same direction. The thinning out/profiling is in this case possible in the same manner as for the straight tufts of bristles. The difference is in the appearance of the tufts of bristles. In the present case, the plane of the higher bristle ends 37 and the plane of the lower bristle ends 38 are no longer perpendicular to the axis of the blind hole 40 in which they have been introduced or in relation to the longitudinal axis of the bristles 21. The planes are in this case parallel to the head area of the toothbrush.

A further configurational possibility is the variable arrangement of the anchors 45. If the toothbrush or the head part 10 is turned correspondingly during the bristle-providing process, the anchors 45 are fixed at different angles in relation to one another in the brush head. The asymmetric punching of the tufts of bristles 20, that is to say the variable arrangement of higher and lower bristle ends 37, 38, is made possible as a result.

A certain discipline is nevertheless necessary, in order that thinning out—as described further above—can take place; this means that the tufts of bristles must be arranged in certain transverse rows. The variable arrangement of the anchors 45, and accordingly of the higher bristle ends 37, makes the thinning out less regular, when considered over the entire bristle area, or the various tufts of bristles are thinned out to different degrees.

The alternative to this, that the anchor positions, and consequently the orientation of the tufts of bristles 20, are varied in the bristle area, is that all the tufts of bristles 20 are oriented identically and no mirror-inversion of the higher bristle ends 37 with respect to the longitudinal axis 29 is obtained.

All the parts of the toothbrush body, that is to say the handle part, the neck part 15 and the head part 10, may be produced from one or more hard components and additionally with one or more soft components. The soft component is optional however.

The production process according to the invention and the toothbrush head according to the invention are not only suitable for handheld toothbrushes but also for vibrating/acoustic toothbrushes or electric toothbrushes with rotating, oscillating, swiveling head parts 10 or with head parts 10 which perform a back and forth movement in the longitudinal direction, or combinations thereof.

It goes without saying that the configurational variants shown and described are given by way of example and the individual refinements and elements of these configurational variants may be combined with other configurational variants without departing from the scope of this invention.

In the case of all the embodiments shown, the tufts of bristles 20 form two bristle tuft halves 35, 36 by the U-shaped bending or folding around the relevant anchor 45. The bristle tuft half 36 has in each case—as a result of the asymmetric folding—only bristles 21 with lower bristle ends 38. The other bristle tuft half 35 has in each case bristles 21 of which the bristle ends 37 stand up higher with respect to the bristle ends 38 of the bristle tuft half 36. In this case, all the bristle ends 37 of the bristle tuft half 35 may stand up higher, as is preferably the case with the embodiments according to FIGS. 15 to 22. However, in addition to the bristles 21 with higher bristle ends 37, the bristle tuft halves 35 may also have ones with lower bristle ends 38, as is shown as a preference in the case of the exemplary embodiments according to FIGS. 1 to 6.

The present invention also concerns a toothbrush with a handle and a bristle-carrying head part 10, which are connected to each other by a neck part 15, the head part 10 having a multiplicity of tufts of bristles 20 consisting of bristles 21, respectively forming two bristle tuft halves 35, 36 and fastened in the head part 10 by means of an anchor 45. The tufts of bristles are arranged along lines that are preferably continuous. The lines extend at a distance from one another that is preferable constant. The lines are preferably concentric circular lines. The anchors 45 of the tufts of bristles 20 run at least approximately, preferably exactly, tangentially in relation to the lines. The one bristle tuft half 35 has bristle ends 37 standing up higher in relation to the bristle ends 38 of the other bristle tuft half 36.

It is preferred in this respect for all the tufts of bristles 20 that are assigned to a line to be aligned identically; the outer bristle tuft half 35, 36 with respect to the line is in each case the one with the lower bristle ends 38 or the one with the higher bristle ends 37.

It is also preferred in this respect for the tufts of bristles 20 that are assigned to all the lines to be aligned identically; the outer bristle tuft halves 35, 36 with respect to the lines are the ones with the lower bristle ends 38 or the ones with the higher bristle ends 37.

It is also preferred in this respect for the tufts of bristles 20 that are respectively assigned to a line to be aligned identically; the outer bristle tuft half 35 or 36 with respect to the relevant line is in each case the one with the lower bristle ends 38 or the one with the higher bristle ends 37. The tufts of bristles 20 assigned to the neighboring line are arranged the other way round in relation to one another. The bristle tuft halves 35 and 36 of the tufts of bristles 20 following one another in the radial direction are consequently facing one another.

The invention claimed is:

1. An electrically operated toothbrush with a longitudinal axis and comprising a handle and a bristle-carrying head part, which are connected to each other by a neck part, the head part performing a rotating or oscillating motion and having a multiplicity of tufts of bristles comprising bristles that are pointed at one end, respectively forming two bristle tuft halves and being fastened in the head part by means of an anchor, wherein the pointed ends of the bristle tufts form higher bristle ends relative to the other ends of the same bristle tuft, at least a part of the tufts of bristles being arranged in rows, in the tufts of bristles that are arranged in rows, the bristles with the higher pointed ends are arranged to be closer to the handle of the toothbrush than the other ends of the same bristle tuft, and the longitudinal axis of the toothbrush is substantially at right angles to the anchors.

2. The toothbrush as claimed in claim 1, wherein the other ends of the bristle tufts comprise rounded ends.

3. The toothbrush as claimed in claim 1, wherein the anchors of the tufts of bristles which are arranged in rows are oriented at least approximately at right angles to a longitudinal axis of the toothbrush.

4. The toothbrush as claimed in claim 1, wherein the anchors of the tufts of bristles which are arranged in rows are oriented at least approximately in parallel to a longitudinal axis of the toothbrush.

5. The toothbrush as claimed in claim 1, wherein in the tufts of bristles which are arranged in rows, the bristles with the pointed ends are positioned at the front, with respect to a longitudinal direction of the toothbrush.

6. The toothbrush as claimed in claim 1, wherein the pointed ends of the bristles of the tufts of bristles which are arranged in rows form parallel rows, with respect to a longitudinal direction of the toothbrush.

7. The toothbrush as claimed in claim 1, wherein the pointed ends of the bristles of the tufts of bristles which are arranged in rows form parallel rows which run perpendicular to a longitudinal axis of the toothbrush.

8. The toothbrush as claimed in claim 1, wherein the head part performs an additional back and forth movement in the longitudinal direction of the toothbrush.

9. The toothbrush as claimed in claim 1, wherein the pointed bristles comprise a nominal diameter of 0.15-0.25 mm and a length, measured from leaving a blind hole of the head part, of 7 to 13 mm, wherein the diameter of the pointed bristles is greater than 75% of the nominal diameter up to a distance of 5 mm measured from the tip.

10. The toothbrush as claimed in claim 1, wherein the tufts of bristles are arranged in at least one circle.

11. The toothbrush as claimed in claim 10, wherein the tufts of bristles are arranged in concentric circles.

12. The toothbrush as claimed in claim 10, wherein the anchors of the tufts of bristles are arranged at an angle of 90°+/−20°.

13. The toothbrush as claimed in claim 10, wherein the pointed ends of the bristles of the bristle tufts are directed towards the center point of the at least one circle.

14. The toothbrush as claimed in claim 10, wherein the pointed ends of the bristles of the bristle tufts are directed away from the center point of the at least one circle.

15. The toothbrush as claimed in claim 10, wherein the pointed bristles comprise a nominal diameter of 0.15-0.25 mm and a length, measured from leaving a blind hole of the head part, of 7 to 13 mm, wherein the diameter of the pointed bristles is greater than 75% of the nominal diameter up to a distance of 5 mm measured from the tip.

16. The toothbrush as claimed in claim 1, wherein anchors of a first part of the tufts of bristles lie at respective tangents to at least two concentric circles formed by center points of the respective bristle tufts and wherein a second part of the tufts of bristles are arranged in rows.

* * * * *